United States Patent
Eckersley et al.

(10) Patent No.: US 11,857,367 B2
(45) Date of Patent: Jan. 2, 2024

(54) ULTRASOUND METHOD AND APPARATUS

(71) Applicant: KING'S COLLEGE LONDON, London (GB)

(72) Inventors: Robert Eckersley, London (GB); Joseph Hajnal, London (GB); Alberto Gomez, London (GB); Laura Peralta Pereira, London (GB)

(73) Assignee: King's College London, London (GB)

(*) Notice: Subject to any disclaimer, the term of this patent is extended or adjusted under 35 U.S.C. 154(b) by 221 days.

(21) Appl. No.: 17/255,806

(22) PCT Filed: Jun. 28, 2019

(86) PCT No.: PCT/GB2019/051855
§ 371 (c)(1),
(2) Date: Dec. 23, 2020

(87) PCT Pub. No.: WO2020/002952
PCT Pub. Date: Jan. 2, 2020

(65) Prior Publication Data
US 2021/0275141 A1    Sep. 9, 2021

(30) Foreign Application Priority Data
Jun. 29, 2018 (GB) .................................. 1810711

(51) Int. Cl.
*A61B 8/00*    (2006.01)
*G01S 15/89*    (2006.01)

(52) U.S. Cl.
CPC .......... *A61B 8/4477* (2013.01); *A61B 8/4483* (2013.01); *G01S 15/8913* (2013.01); *G01S 15/8929* (2013.01); *G01S 15/8993* (2013.01)

(58) Field of Classification Search
CPC .............. A61B 8/4483; G01S 15/8913; G01S 15/8929; G01S 15/8993
See application file for complete search history.

(56) References Cited

U.S. PATENT DOCUMENTS 8,002,705 B1*   8/2011   Napolitano .......... A61B 8/5246
                                             600/407
9,538,987 B2*   1/2017   Hoctor ................ G01S 7/52047
(Continued)

FOREIGN PATENT DOCUMENTS

WO    2015/038525    3/2015

OTHER PUBLICATIONS

Peralta Laura et al.: "Feasibility Study 1-17 of a Coherent Multi-Transducer US Imaging System," 2018 IEEE International Ultrasonics Symposium (IUS), IEEE, Oct. 22, 2018 (Oct. 22, 2018), pp. 1-4, XP033480056, United States.
(Continued)

*Primary Examiner* — Dixomara Vargas
(74) *Attorney, Agent, or Firm* — Keller Preece PLLC

(57) ABSTRACT

Embodiments described provide an ultrasound method, and an ultrasound apparatus and computer program product operable to perform that method. In some embodiments, the method allows for provision of a multi-transducer ultrasound imaging system by providing a robust method to accurately localize the transducers in the system in order to beamform a final image. The method and apparatus described allow for improvements in imaging quality in terms of resolution, depth penetration, contrast and signal to noise ratio (SNR).

13 Claims, 19 Drawing Sheets

(56) References Cited

U.S. PATENT DOCUMENTS

| | | | | |
|---|---|---|---|---|
| 2012/0083695 | A1* | 4/2012 | Napolitano | G10K 11/341 600/443 |
| 2013/0079639 | A1* | 3/2013 | Hoctor | G01S 7/52025 600/447 |
| 2014/0378834 | A1* | 12/2014 | Napolitano | A61B 8/463 600/443 |
| 2015/0080727 | A1 | 3/2015 | Specht et al. | |
| 2015/0241397 | A1* | 8/2015 | Savord | G01N 29/24 600/459 |
| 2015/0297183 | A1* | 10/2015 | Freeman | G01S 7/5208 600/459 |
| 2015/0359512 | A1 | 12/2015 | Boctor et al. | |
| 2018/0003810 | A1* | 1/2018 | Freeman | G01S 7/52095 |
| 2020/0064468 | A1* | 2/2020 | Holbek | G01S 15/8993 |
| 2021/0353253 | A1* | 11/2021 | Da Cruz | A61B 8/12 |
| 2022/0117584 | A1* | 4/2022 | Haider | A61B 8/4494 |
| 2022/0378399 | A1* | 12/2022 | Salgaonkar | B06B 1/0622 |

OTHER PUBLICATIONS

Peralta Laura et al: "Coherent Multi-Transducer Ultrasound Imaging", arxiv, Mar. 5, 2019 (Mar. 5, 2019), pp. 0-14, XP055648303, Retrieved from the Internet: URL:https://arxiv.org/pdf/1903.01934.pdf [retrieved on Dec. 2, 2019], United States.

Boni Enrico et al.: "ULA-OP 256: A 256-Channel Open Scanner for Development and Real-Time Implementation of New Ultrasound Methods," IEEE Transactions on Ultrasonics, Ferroelectrics and Frequency Control, IEEE, vol. 63, No. 10, Oct. 1, 2016 (Oct. 1, 2016), pp. 1488-1495, XP011624448, United States.

Application No. GB1810711.0 Search Report under Section 17 dated Dec. 18, 2018, 3 pages.

* cited by examiner

ULTRASOUND METHOD AND APPARATUS

FIELD OF THE INVENTION

Aspects and embodiments described provide an ultrasound method and an ultrasound apparatus and computer program product operable to perform that method.

BACKGROUND

Ultrasound is a widely used analysis tool. Advantages of ultrasound include safety and low cost compared to other possible analysis tools. However, conventional ultrasound systems can yield information which may be difficult to assess, for example, as a result of limited resolution and view-dependent artefacts that are inherent to ultrasound transducers typically used. Ultrasound imaging using typical ultrasound transducers can be particularly challenging, for example, if seeking to image at large depths.

SUMMARY

A first aspect provides an ultrasound method comprising: configuring two or more separate ultrasound transmitters to transmit a signal into a coincident region; configuring a receiving array to receive wavefronts representative of a transmitted signal from each of the two or more transmitters after interaction of the transmitted signal with a medium located within the coincident region; analysing each of the received wavefronts to determine a relative spatial position of each of the two or more separate ultrasound transmitters; and using the determined relative spatial position of each of the two or more separate ultrasound transmitters to perform coherent signal combination of the wavefronts received at the receiving array from each of the two or more transmitters after interaction of the transmitted signal with the medium located within the coincident region.

Various mechanisms to improve data collected using ultrasound techniques are known. Such mechanisms include, for example, compound data collection methods and system arrangements, extended field of view methods and system arrangements and arrangements which operate to increase an effective aperture of an ultrasound data collection system.

The first aspect recognises that a typical ultrasound transducer, comprising a transmitting array and a receiving array, is usually dimensioned for a particular application. For example, in a clinical or medical environment, a transducer is dimensioned to allow for an operator to hold and move the transducer and the shape and size of the transducer is such that it can maintain contact with the surface of a human or animal body as it is moved around the surface of that body. Other applications of ultrasound can have similar limitations regarding physical dimensions of an ultrasound transmitter and/or receiver. As a result of physical constraints, data which can be collected via ultrasound techniques may be subject to limitations. It is well recognised, for example, in optical and radio frequency systems, that increasing the effective aperture can improve an image created from collected data.

Creation of an extended aperture ultrasound system may be limited by complexity, expense and ultrasound transducers having large physical dimensions to allow for a large aperture have a limited adaptability to different applications.

The first aspect recognises that it may be possible to implement a method, using simple ultrasound components, which allows for one or more of the challenges in ultrasound applications to be addressed. A method according to the first aspect recognises that one of the challenges in an ultrasound system can be accurate and precise location of transmitting and receiving elements in that system. The first aspect provides a method for location of key elements in a system, based on information collected by the ultrasound system. In particular, rather than needing to know or maintain a particular physical positioning of one or more elements forming an ultrasound system, the first aspect provides a method to determine physical positioning by using ultrasound waves transmitted and received by elements of the system at the same time that the elements are operating to collect information about a medium under study using ultrasound methods. A method according to the first aspect may provide a mechanism to both determine the position of key operational elements of an ultrasound system and, having determined those positions, interpretation of data collected by the ultrasound system may be improved.

The first aspect provides an ultrasound method. That ultrasound method may comprise a medical or clinical ultrasound method. The ultrasound method may comprise a medical ultrasound imaging method. The method may comprise a step comprising: configuring two or more separate ultrasound transmitters to transmit a signal into a coincident region. Those transmitters may comprise a point transmitter or transmitting element or transmitting array. The transmitting array may comprise a plurality of transmitting elements. In either instance, the signal transmitted by the two or more ultrasound transmitters passes through an at least partly overlapping, or coincident region. That region may comprise an imaging region, into which a medium to be studied may be placed.

The method of the first aspect may comprise a step of: configuring a receiving array to receive wavefronts representative of a transmitted signal from each of the two or more transmitters after interaction of the transmitted signal with a medium located within the coincident region. The receiving array may comprise a plurality of receiver elements configured to receive the signals transmitted after they have been scattered by the medium under study. The method may comprise a step of analysing each of the received wavefronts received by the receiving array. That analysing of the form of the received wavefronts at the receiving array can allow for determination of a relative spatial position of each of the two or more separate ultrasound transmitters. Analysing each of the wavefronts received by the receiving array may comprise analysing one or more wavefront received at the receiving array based on a signal transmitted by a first ultrasound transmitter and analysing one or more wavefront received at the receiving array from a second ultrasound transmitter. The wavefronts received from the first and second ultrasound transmitters may be compared.

The method may then comprise using the determined relative spatial position of each of the two or more separate ultrasound transmitters to perform coherent signal combination of the wavefronts received at the receiving array from each of the two or more transmitters after interaction of the transmitted signal with the medium located within the coincident region. Accordingly, by analysing received wavefronts over a temporal window to determine relative spatial position of the separate ultrasound transmitters it becomes possible to perform a coherent signal combination and therefore potentially obtain an improved image of a medium within the coincident region.

The method of the first embodiment may be performed with as few as two, effectively separate, ultrasound transmitters. The transmitters may be distinct remote and/or physically separate. The receiving array may be co-located with a transmitter or may be remote from the transmitters.

The first aspect recognises that using the ultrasound signals themselves to calculate the relative positions of the transmitters means that there is no need to precisely know, for example, using translation stage equipment or similar, or restrain, the physical positions of ultrasound transmitters in space. The significant requirement is that the signals from the transmitters, received at the receiving array, at least partly overlap in a region of interest. In other words, provided the transmitters are directed towards an identical (overlapping) volume of medium of interest, it is possible to make use of the method of the first aspect and use the ultrasound signals received at the receiving array to determine the positioning of the transmitters.

In one embodiment, the analysing comprises: selecting one or more parameters defining the relative spatial position of each of the two or more separate ultrasound transmitters. Accordingly, any set of parameters which together act to define a location of the transmitters in space can be selected. In one embodiment, a selection of a set of parameters is made, together with a set of possible ranges for each parameter. An initial "seed" guess within the relevant range offering relative transmitter location may be used as a starting position for then implementing an optimisation method in accordance with the first aspect.

In one embodiment, the analysing comprises: using the received wavefronts to make an initial guess at one or more parameters defining the relative spatial position of each of the two or more separate ultrasound transmitters. That is to say, a coarse guess of relative transmitter location can be made, that guess being made in dependence upon received wavefronts. For example, wavefronts received from each transmitter from a scatterer within a medium may be identified. Since the difference in receive time between the two received wavefronts scattered by the same scatterer will attributable to a difference in transmitter to common-scatterer transit time, an estimate of distance can be made.

In one embodiment, the analysing comprises: receiving an indication of one or more parameters defining the relative spatial position of each of the two or more separate ultrasound transmitters from one or more orientation sensors provided at each ultrasound transmitter. Accordingly, an initial guess, which can be refined by means of an approach in accordance with the first aspect, can be provided by physical positioning sensor(s) provided. Those sensors may be located on a transmitter body, for example.

In one embodiment, the parameters comprise: a combination of one or more parameters which allow the relative spatial position of each of the two or more separate ultrasound transmitters to be determined. Accordingly, a combination of angle and distance and other similar parameters may be selected.

In one embodiment, the parameters comprise: one or more of: location of one or more scatterer located within the medium located within the coincident region; relative angle between the ultrasound transmitters; relative distance of the ultrasound transmitters from the receiving array; speed of sound within the medium located within the coincident region. In one embodiment, the parameters consist of: location of one or more scatterer located within the medium located within the coincident region; relative angle between the ultrasound transmitters; relative distance of the ultrasound transmitters from the receiving array; speed of sound within the medium located within the coincident region or equivalents thereof.

In one embodiment, the analysing comprises: increasing correspondence between the received wavefronts by refining the parameters defining the relative spatial position of each of the two or more separate ultrasound transmitters. In one embodiment, the correspondence comprises: a correlation between the received wavefronts. Accordingly, an iterative process is used to perform the analysing step of a method of the first aspect. Various criteria can be used to "stop" the iterative or refining process. The stopping criteria may comprise a selected number of iterations. The stopping criteria may comprise a measure of fit passing a selected threshold value. The stopping criteria may comprise a maxima or minima or rate of change of a fit parameter reaching a plateau.

In one embodiment, the method further comprises: using the refined parameters to select the relative spatial position to be used when performing the coherent signal combination. Accordingly, once a refined spatial position of the transmitters is calculated, then coherent signal combination of the information received at the receiving array from each transmitter can be performed. That is to say, it is possible to match received signals at the receiving array from the two or more ultrasound transmitters.

Some implementations of the first aspect may provide an ultrasound method comprising: configuring two or more separate ultrasound transmitters to transmit a signal into a coincident region; configuring a receiving array to receive wavefronts representative of a transmitted signal from each of the two or more transmitters after interaction of the transmitted signal with a medium located within the coincident region; analysing each of the received wavefronts to determine an indication of a relative spatial position of each of the two or more separate ultrasound transmitters; and using the determined indication of relative spatial position of each of the two or more separate ultrasound transmitters to calculate one or more properties of the medium located within the coincident region. In some embodiments, the one or more properties may comprise a speed of sound signal within (sub)areas of the medium. In some embodiments, the one or more properties may comprise a density map of areas of the medium. It will be appreciated that wavefront aberration caused by an inhomogeneous medium can limit the quality of ultrasound images and is one significant barrier to achieving diffraction-limited resolution with large aperture transducers [18]. One implementation of a method in accordance with the first aspect may assume the speed of sound is constant along a propagation path. However, since the speed of sound is a parameter which may be optimised in some embodiments, the method described can be adapted to apply to non-homogeneous media in which the speed of sound varies in space. In such a case, for example, the medium could be modelled by piecewise continuous layers. The optimization method could be applied in a recursive manner, dividing a FoV into appropriate sub areas with different speeds of sound. More accurate speed of sound estimation may allow for improved beamforming and allow for higher order phase aberration correction. Furthermore, speed of sound maps within a medium can be of use in tissue characterization.

Implementations of the first aspect allow a system which avoids a need for pre-calibration and/or prior knowledge of relative location of the two or more separate ultrasound transmitters arranged to transmit a signal into a coincident region. In particular, rather than needing to perform a direct transmission from transmitter to receiver in order to calculate relative position of transmitter and receiver, it is possible to use data obtained from a scattering medium under study to calculate relative positions of the transmitters. Implementations using scatterers within a medium under study to determine relative positioning of the transmitters represent an efficient mechanism to ensure that the geometry is always favourable (provided there is a coincident region).

Some implementations of the first aspect provide a method of using shared information, for example, prominent scatterers or other prominent features in received cross-transducer data to enable localisation of apertures, even without the presence of clear point targets within a medium under study. In some arrangements, an exogeneous source of prominent scatterers, for example, a low concentration of microbubbles, can be used to assist correlation between received cross-transducer data.

Implementations of the first aspect recognise that whilst typical apertures (formed within each individual transmitter/receiver array) may be subject to a maximum useable size set by the dispersion of the speed of sound within a medium under study, some embodiments may comprise a "super aperture" formed from multiple transmitter/receiver arrays and the super aperture is not subject to that same maximum size constraint.'

A second aspect provides a computer program product operable, when executed on a computer, to perform the ultrasound method of the first aspect.

A third aspect provides ultrasound apparatus comprising: two or more separate ultrasound transmitters configured to transmit a signal into a coincident region; a receiving array configured to receive a wavefront representative of a transmitted signal from each of the two or more transmitters after interaction of the transmitted signal with a medium located within the coincident region; location processing logic configured to analyse each of the received wavefronts and determine a relative spatial position of each of the two or more separate ultrasound transmitters; and signal combination logic configured to use the determined relative spatial position of each of the two or more separate ultrasound transmitters to perform coherent signal combination of the wavefronts received at the receiving array from each of the two or more transmitters after interaction of the transmitted signal with the medium located within the coincident region.

In one embodiment, the two or more separate ultrasound transmitters are located such that their signal volumes at least partly overlap within the coincident region. In other words, said two or more separate ultrasound transmitters are located such that a field or cone of view of each of the separate ultrasound transmitters at least partly overlaps with a field of view of each other of the transmitters within said coincident region.

In one embodiment, the ultrasound signal comprises a pulsed ultrasound signal. The repetition rate of the ultrasound pulses can be dependent upon the depth within a medium of interest to be imaged. A higher pulse frequency offers higher temporal sampling of a medium under study.

In one embodiment, the two or more separate ultrasound transmitters are configured to transmit a signal into the coincident region substantially concurrently. In one embodiment, the two or more separate ultrasound transmitters are configured to transmit a signal into the coincident region consecutively. Depending upon application, an appropriate transmission mode may be selected. Concurrent transmissions may increase computational complexity yet allow for increased sensitivity in the information collected by a receiving array.

In one embodiment, the signal transmitted by each of the two or more transmitters comprises a plane wave. In one embodiment, the signal transmitted by each of the two or more transmitters comprises a point ultrasound source. In one embodiment, the transmitted signal comprises a known wave configuration. The transmitted signal may comprise any reasonable known wave configuration, for example, a sine wave, or similar.

In one embodiment, the apparatus further comprises: at least one further receiving array configured to receive the wavefront representative of a transmitted signal from each of the two or more transmitters after interaction of the transmitted signal with the medium located within the coincident region; and wherein the location processing logic is configured to analyse each of the received wavefronts received at each receiving array and determine a relative spatial position of each of the two or more separate ultrasound transmitters; and wherein the signal combination logic is configured to use the determined relative spatial position of each of the two or more separate ultrasound transmitters from each receiving array to perform coherent image reconstruction of the medium located within the coincident imaging region by combining wavefronts received at each the receiving array from each of the two or more transmitters after interaction of the transmitted signal with a medium located within the coincident region. Accordingly, it may be possible to perform the same analysis using two or more receiving arrays, thus effectively increasing the receive aperture.

In one embodiment, at least one of the two or more separate ultrasound transmitters and one or more of the receiving arrays are co-located to form an ultrasound transducer. In one embodiment, each of the two or more separate ultrasound transmitters and receiving arrays are co-located to form an ultrasound transducer.

Further particular and preferred aspects are set out in the accompanying independent and dependent claims. Features of the dependent claims may be combined with features of the independent claims as appropriate, and in combinations other than those explicitly set out in the claims. In particular, features of the first aspect may be incorporated appropriately into the third aspect and vice versa.

Where an apparatus feature is described as being operable to provide a function, it will be appreciated that this includes an apparatus feature which provides that function, or which is adapted or configured to provide that function.

BRIEF DESCRIPTION OF THE DRAWINGS

Embodiments of the present invention will now be described further, with reference to the accompanying drawings, in which.

DESCRIPTION OF THE EMBODIMENTS

Figure 1:
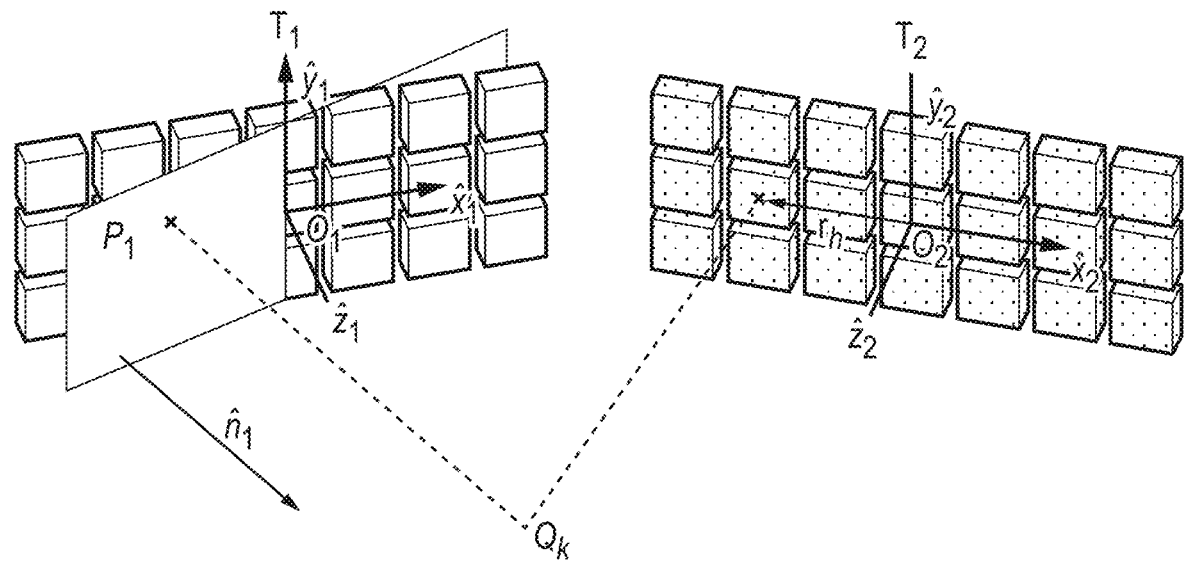
FIG. 1 is a geometric representation of a multi-transducer beamforming scheme.

Before describing one particular embodiment in detail, a general overview of methods and devices utilising concepts described is provided.

It is recognised throughout imaging systems that an extended aperture has potential to improve imaging performance [1]. When using ultrasound as an analysis tool, particularly in a clinical context, aperture size can be limited by complexity and expense associated with an extended aperture system. Furthermore, ultrasound transducers having large physical dimensions to allow for a large aperture have a limited adaptability to different applications.

Taking as one example, clinical use of ultrasound for imaging, typical clinical ultrasound probes are controlled and moved by a physician to adapt to contours and shapes of a human body. Physical ultrasound transducer size becomes a compromise between cost, ergonomics and image performance. Providing a method by which ultrasound image quality may be improved without altering dimensions of conventional ultrasound probes may be useful.

Improvements associated with a wider coherent aperture have been shown in synthetic aperture ultrasound imaging [2], [3]. In those arrangements, an extended aperture is obtained by mechanically moving and tracking an ultrasound transducer. Detailed position and orientation tracking information is used to identify a relative position and orientation of obtained ultrasound images which are then merged together into a final image [4]. However, tracking system noise and calibration errors propagate to coherent image reconstruction, causing image degradation. In practical terms, subwavelength localization accuracy is required to merge information from multiple poses. Such accuracy is challenging to achieve in conventional ultrasound calibration. For a practical implementation, a more accurate calibration technique is required [3], [5]. In addition, viability of the technique in-vivo is limited by long acquisition times (>15 minutes per image) which may break down a coherent aperture [6]. Resolution suffers from motion artefacts, tissue deformation and tissue aberration, all of which worsen with increased effective aperture size [7].

Methods according to some aspects and embodiments may provide a fully coherent multi-transducer ultrasound imaging system. That system can be formed from a plurality of ultrasound transducers which are synchronized, freely disposed in space and configured to transmit plane waves (PW). By coherently integrating different transducers a larger effective aperture, in both transmit and receive, can obtained and an improved final image can be formed. As described previously, coherent combination of information obtained by the different transducers requires the position of transmitters and receivers within the system to be known to subwavelength accuracy.

In general, a method is described which can achieve an accurate subwavelength localization of ultrasound transmitters (and receivers) within a multi-transmitter system. Based on a spatial coherence function of backscattered echoes originating from a common point source received by the same transducer; multiple transducers of a multi-transducer ultrasound imaging system can be localized without use of an external tracking device. Using plane waves (PW) generates a higher energy wavefield than in a synthetic aperture approach, therefore improving penetration. Use of PW also enables higher frame rates [8].

The principles of classic PW imaging are summarized below together with nomenclature used and an overview of multiple transducer beamforming. A method to accurately calculate the spatial location of the different transducers is described. Experimental phantom measurements are described and corresponding results, obtained using a multi-transducer system, are shown. Results are compared to conventional PW imaging using a single transducer and incoherently compounded images from the plurality of transducers.

Theory

Ultrasound image quality improves by reducing the F number, which represents a ratio of focusing depth to an aperture size. Expanding an aperture is a direct way to improve imaging performance. Hence, if information from different transducers can be coherently combined, significantly increasing aperture size of a system, an enhanced image is expected.

In one possible coherent multi-transducer method, a single transducer is used for each transmission to produce a plane wave (PW) that isolates an entire Field of View (FoV) of the transmit transducer. Resulting echoes scattered from a medium are recorded using all transducers forming part of the multi-transducer system. A data collection sequence is performed by transmitting from each individual transducer in turn. Knowing the location of each transducer (and taking into account full transmit and receive path lengths) coherent summation of collected data from multiple transducers can be used to form a larger aperture and obtain image, following a conventional PW imaging approach.

Multi-Transducer Notation and Beamforming

A 3-D framework consisting of N matrix arrays, freely disposed in space, having a partly shared field of view (FoV) is considered. Such a framework represents positioning of a plurality of ultrasound transducers. Other than an at least partly overlapping field of view, the transducers can be considered to be otherwise at arbitrary positions in space. The transducers are synchronized (in other words, in this arrangement, trigger and sampling times in both transmit and receive mode of the ultrasound transducers are the same). The ultrasound transducers are configured to take turns to transmit a plane wave into a medium. The arrangement is such that each transmitted wave is received by all transducers, including the transmitting one. Thus, a single plane wave shot yields N RF datasets—one associated with each receiving transducer.

The framework is described using the following nomenclature:

Points are noted in upper case letters (e.g. P);
Vectors representing relative positions are represented in bold lowercase (e.g. r);
Unit vectors are noted with a "hat"; and
Matrices are written in bold uppercase (e.g. R).

Index convention is to use i for the transmitting transducer, j for the receiving transducer, h for transducer elements, and k for scatterers. Other indices are described when used.

The set-up be defined by N matrix array transducers $T_i$, i=1 . . . N, with H elements as illustrated in FIG. 1. The position and orientation of $T_i$ is represented by the axes $\{\hat{x}_i; \hat{y}_i; \hat{z}_i\}$ and the origin $O_i$ defined at the centre of the transducer surface with the $\hat{z}_i$ direction orthogonal to the transducer surface and directed away from transducer i. A plane wave transmitted by transducer $T_i$ is defined by the plane $P_i$, which can be characterized through the normal to the plane $\hat{n}_i$, and the origin $O_i$. The RF data received by transducer j on element h at time t is noted $T_iR_j(h; t)$. The resulting image and all transducer coordinates are defined in a world coordinate system arbitrarily located in space, unless specifically referred to a transducer's local coordinate system in which case the superscript i is used.

FIG. 1 is a geometric representation of a multi-transducer beamforming scheme. In the example shown in FIG. 1, transducer $T_1$ transmits a plane wave and $T_2$ receives the echo scattered from $Q_k$ on element h. Using the notation set out above, plane wave imaging beamforming [8] can be extended to the multi-transducer scheme shown in FIG. 1. Assuming that transducer Ti transmits a plane wave, the image point to be beamformed located at $Q_k$ can be computed from the echoes received at transducer $T_j$ as:

$$s_{i,j}(Q_k) = \sum_{h=1}^{H} T_i R_j(h, t_{i,h,j}(Q_k)) = \sum_{h=1}^{H} T_i R_j\left(h, \frac{D_{i,h,j}(Q_k)}{c}\right) \quad (1)$$

where c is the speed of sound of the medium, and D is the distance travelled by the wave, which can be split into the transmit and the receive distances:

$$D_{i,h,j}(Q_k) = d_T(Q_k, P_i) + d_{R,h}(Q_k, O_j + r_h) \quad (2)$$

with $d_T$ measuring the distance between a point and a plane (transmit distance), and $d_{R,h}$ being the distance between a point and the receive element (receive distance). These distances can be computed as follows:

$$d_T(Q_k, P_i) = |(O_i - Q_k) \cdot \hat{n}_i| \quad (3)$$

and $$d_{R,h}(Q_k, O_j + r_h) = \|Q_k(O_j + r_h)\| = \|Q_k - (O_j + R_j r_h^j)\| \quad (4)$$

where $\|\ \|$ is the usual Euclidean distance, and $Rj = [\hat{x}_j\ \hat{y}_j\ \hat{z}_j]$ is a 3×3 matrix parameterized through three rotation angles:

$$\emptyset_j = \{\emptyset_x, \emptyset_y, \emptyset_z\}j$$

that together with the offset $O_j$ characterize the position and orientation of transducer $T_j$ with 6 parameters [9].

With the total distances computed, equation (1) can be evaluated for each pair of transmit-receive transducers, and the total beamformed image $S(Q_k)$ can be obtained by coherently adding the individually beamformed images:

$$S(Q_k) = \sum_{i=1}^{N} \sum_{j=1}^{N} s_{i,j}(Q_k) \quad (5)$$

Calculation of the Transducer Locations

In order to carry out the coherent multi-transducer compounding described above, the position and orientation of each imaging transducer is required. This then allows for computation of travel time of a transmitted wave to any receiving transducer. This section describes one method to accurately calculate those positions by exploiting consistency of received RF data when transducers receive simultaneously from the same transmitted (and scattered) wave. The method described assumes the medium is substantially homogeneous except for K point scatterers located at positions $Q_k$, k=1 . . . K, and all transducers are considered identical.

The following transmit sequence is considered:

a plane wave is transmitted by transducer $T_i$ and received by N transducers forming the multi-transducer system;
a plane wave is transmitted by $T_j$ and also received by all transducers; the process continues until the N transducers have transmitted in turn.

During the time during which each transmitter operates in turn, it is assumed that the system and medium under study remain perfectly still.

The wavefield resulting from the same scatterer and received by the same transducer $T_j$, when transmitting with all transducers, must be correlated or have spatial covariance [10]. That is to say, for each element h, the only difference in timing is the transmit time (receive time is equal since the receiving transducer is the same). The received signals at the element h will be time correlated when the difference in transmit time is compensated for.

One method comprises finding the "optimal" parameters for which the time correlation between received RF datasets sharing a receive transducer is at a maximum for all scatterers in the common FoV.

Since the reception time depends also on the speed of sound in the medium c and on the position of the scatterers $Q_k$, the unknown parameters are:

$$\theta = \{c, Q_1, \ldots, Q_K, \phi_1, O_1, \ldots, \phi_N, O_N\} \quad (6)$$

Note that, since the parameters that define transducer locations in space depend on the definition of the world coordinate system, the vector of unknown parameters can be reduced by defining the world coordinate system the same as the local coordinate system of one transducer.

The similarity between signals received by the same element can be computed using the normalized crossed correlation NCC, $$NCC(y_{i,h,j,k}(\tau), y_{j,h,j,k}(\tau)) = \frac{\sum_{\tau=0}^{T}(y_{i,h,j,k}(\tau) - \bar{y}_{i,h,j,k}(\tau))(y_{j,h,j,k}(\tau) - \bar{y}_{j,h,j,k}(\tau))}{\left[\sum_{\tau=0}^{T}(y_{i,h,j,k}(\tau) - \bar{y}_{i,h,j,k}(\tau))^2 \sum_{\tau=0}^{T}(y_{j,h,j,k}(\tau) - \bar{y}_{j,h,j,k}(\tau))^2\right]^{\frac{1}{2}}} \quad (7)$$

where $y_{i;h;j;k}$ represents the signal backscattered from $Q_k$ and received by element h on transducer j when transmitting from $T_i$, and can be calculated as:

$$y_{i,h,j,k}(\tau;\theta) = T_i R_j(h, \tau + t_{i,h,j}(Q_k;\theta)) \text{ with } \tau \in [0,T] \quad (8)$$

being T the time transmit pulse length.

Then, the total similarity, $X_{j,k}$, between RF data received by the same transducer j can be calculated taking into account all the elements as:

$$X_{j,k}(\theta) = \sum_i^N \sum_h^H NCC(G_{i,h,j,k}(\tau;\theta), G_{j,h,j,k}(\tau;\theta)) W_{i,h,j,k}(\theta) W_{j,h,j,k}(\theta) \quad (9)$$

where $$G_{i,h,j,k} = \sqrt{y_{i,h,j,k}^2 + \mathcal{H}\{y_{i,h,j,k}\}^2}$$

is the envelope of the signal $y_{i,h,j,k}$
$\mathcal{H}$ is the Hilbert transform;
and $W_{i,h,j,k}$ is defined as:

$$W_{i,h,j,k}(\theta) = \frac{1}{2} + \frac{1}{2H} \sum_{\substack{h_b=1 \\ h_b \neq h}}^{H} NCC(y_{i,h,j,k}(\tau;\theta), y_{i,h_b,j,k}(\tau;\theta)) \text{ with } h,$$

$$h_b \in [1, \ldots, H]$$

The function $W_{i,h,j,k}$ is an element-wise weight that represents how well each element correlates with the rest of the elements in the same transducer j.

If intra-transducer channel correlation is not considered, the undesired scenario where the wave receive times are erroneous but in a similar manner for different transmitting transducers could yield to a low dissimilarity value for the wrong parameters.

Summing over all receiving transducers and scatterers yields a final cost function to be maximized:

$$X(\theta) = \sum_j^N \sum_k^K X_{j,k}(\theta) \quad (11)$$

The "optimal" parameters $\bar{\theta}$, which include: relative position and orientation of all transducers involved, the speed of sound in the medium, and the position of the scatterers within the medium, can be found by applying a search algorithm that maximizes the cost functional X:

$$\bar{\theta} = \underset{\theta}{\operatorname{argmax}} X(\theta) \quad (12)$$

Equation (12) can be maximized by using gradient-based optimization methods [11].

Methods

Figure 2:
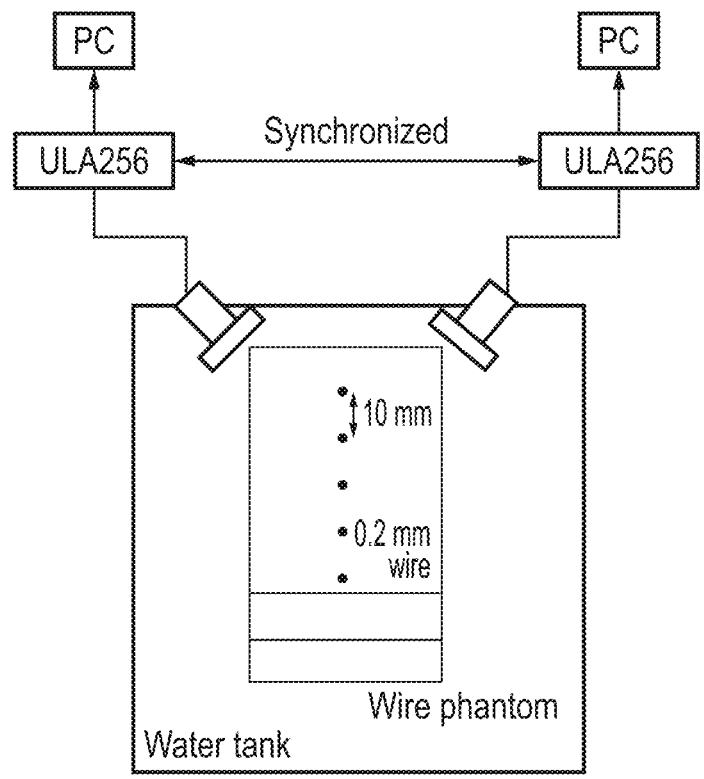
FIG. 2 illustrates schematically an experimental setup comprising two ultrasound transducers.

FIG. 2 illustrates schematically an experimental setup comprising two ultrasound transducers. The method was tested experimentally using 2 identical linear arrays having a partly shared field of view (FoV) of an ultrasound phantom. The identical linear arrays were located on the same plane (y=0). In such a 2-D framework, the parameters that define the position and orientation of the transducers are reduced to one rotation angle and one 2-D translation [9].

The experimental sequence starts with transducer 1 transmitting a plane wave into the region of interest, in which 5 scatterers are located in the common FOV of transducers 1 and 2.

The backscattered ultrasound field is received by both transducers in the system ($T_1R_1$ and $T_1R_2$). Under the same conditions, the sequence is repeated, transmitting with transducer 2 and acquiring the backscattered echoes with both transducers, $T_2R_1$ and $T_2R_2$.

Phantom

Acquisitions were performed on a custom-made wire target phantom (200 µm diameter) submersed in distilled water. The phantom was positioned within the overlapping imaging region of the transducers, so that all scatterers were in the common FoV.

Experimental Setup

The experimental setup comprises two synchronized 256-channel Ultrasound Advanced Open Platform (ULA-OP 256) systems (MSD Lab, University of Florence, Italy) [12]. Each ULA-OP 256 system was used to drive an ultrasonic linear array made of 144 piezoelectric elements with a 6 dB bandwidth ranging from 2 MHz to 7.5 MHz (imaging transducer LA332, Esaote, Firenze, Italy). Before acquisition, probes were carefully aligned to be located in the same elevational plane using a precise optomechanical setup. Each probe was held by a 3-D printed shell structure connected to a double-tilt and rotation stage and then mounted on a xyz translation and rotation stage (Thorlabs, USA). The imaging plane of both transducers (y=0) was that defined by two parallel wires immersed in the water tank.

Figure 3:
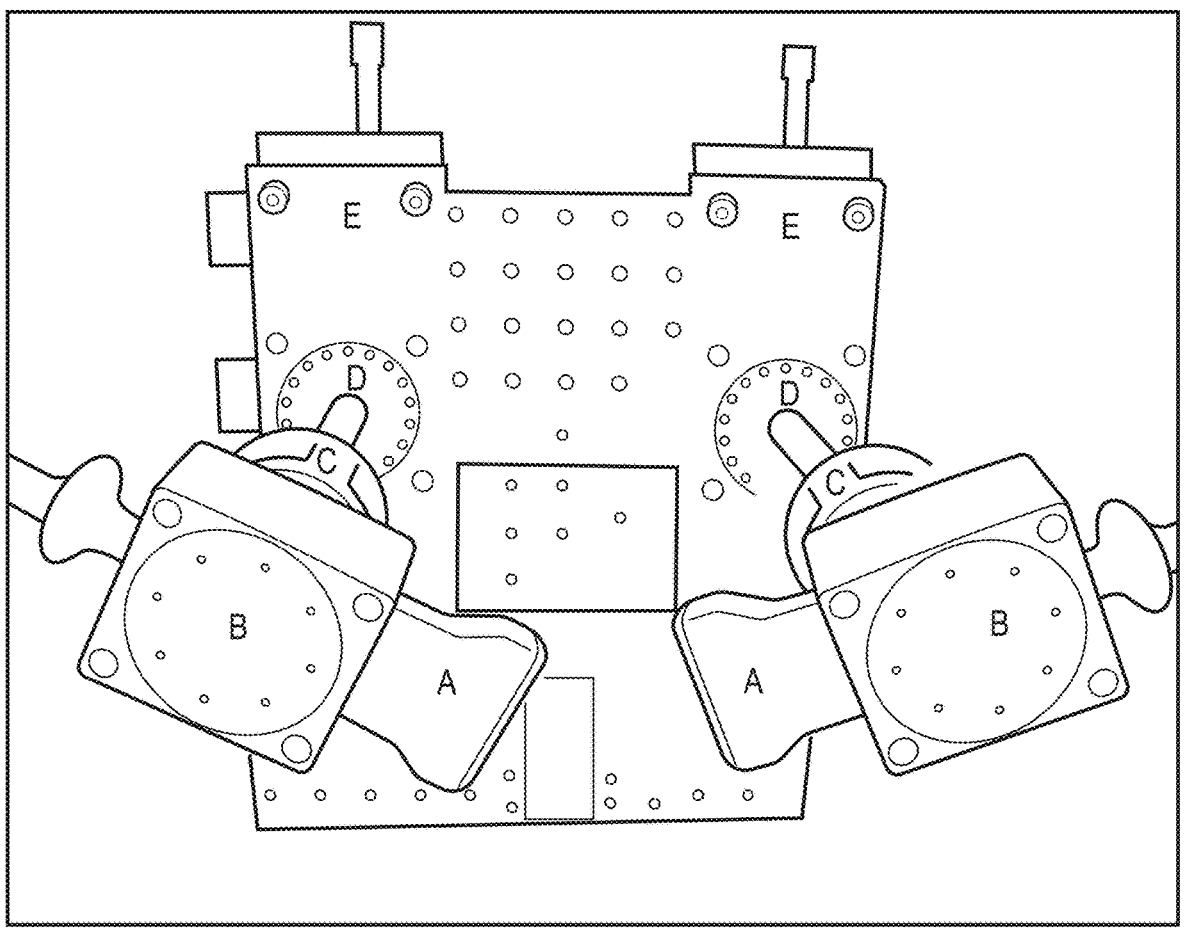
FIG. 3 illustrates the experimental setup of FIG. 2 in more detail.

FIG. 3 illustrates the experimental setup of FIG. 2 in more detail. Components shown in FIG. 3 are labelled with letters: (A) Linear array. (B) 3-D printed probe holder. (C) Double-tilt and rotation stage. (D) Rotation stage. (E) xyz translation stage.

Pulse Sequencing and Experimental Protocol

Two independent experiments were carried out. First, a stationary acquisition in which both probes were mounted and fixed in the optomechanical setup described above. The second experiment consisted of a free-hand demonstration. In this case, both probes were held and controlled by an operator. The transducer movements were carefully restricted to the same elevational plane, i.e. y=0 and to keep two common targets in the shared FoV.

Two different types of pulse sequences were used.

During the stationary experiment, for each probe and at alternating sequence, i.e. only one transducer transmits at each time while both probes receive, 121 plane waves, covering a total sector angle of 60° (from −30° to 30°, 0.5° step), were transmitted from the 144 elements of each probe at 3 MHz with a pulse repetition frequency equal to 4000 Hz. The total sector angle between transmitted plane waves was chosen approximately the same as the angle defined between the probes. RF raw data scattered up to 77 mm deep were acquired at a sampling frequency of 39 MHz. No apodization was applied either on transmission or reception. The total time for this sequence was 6o.5 ms.

During the free-hand demonstration, 21 plane angles (from −5° to 5°, 0.5° step) were transmitted from each probe and RF raw data backscattered up to 55 mm deep were acquired. The remaining settings were identical to the fixed probe experiment. The total acquired time using this sequence was 1 s.

Data Processing

An initial estimate of parameters $$\theta_0 = \{c, Q_1, \ldots, Q_K, \phi_1, O_1, \phi_2, O_2\}$$

needed to start the optimization algorithm was chosen as follows:

The speed of sound of the propagation medium was chosen according to the literature, in the case of water this is c=1496 m/s [13].

Considering the world coordinate system to be the same as the local coordinate system of transducer 1 ($\phi_1=0$, $O_1=[0, 0]$) the parameters $\{\phi_2, O_2\}$ that define the position of transducer 2 were calculated by using point-based image registration [14].

For the scatterer positions $Q_k$, their initial value was calculated using a best-fit one-way geometric delay for the echoes returning from the targets, as described in [15].

Optimization was done using all the targets within the shared FoV.

For the stationary experiment, since there was no motion, only one set of optimal parameters is needed and all RF data corresponding to plane waves transmitted at different angles can be beamformed using the same optimal parameters. However, to validate the optimization algorithm, 121 optimal parameter sets were calculated, one per transmit angle.

For the free-hand demonstration, each frame was generated using a different set of optimal parameters, where each subsequent optimization was initialized with the optimum value of the previous frame. The proposed method was compared with the conventional B-mode imaging using one single transducer and with the incoherent compounding of the B-mode images acquired by two independent transducers. The images acquired during the stationary experiment were used for this image performance analysis. A final image was obtained using equation (5), by coherently adding the totality of the individual images acquired in one sequence ($T_1R_1$, $T_1R_2$, $T_2R_1$, $T_2R_2$):

$$S(Q_k) = s_{1,1}(Q_k) + s_{1,2}(Q_k) + s_{2,1}(Q_k) + s_{2,2}(Q_k) \tag{13}$$

Spatial resolution was calculated from the point spread function (PSF) on a single scatterer. An axial-lateral plane for 2-D PSF analysis was chosen by finding the location of the peak value in the elevation dimension from the envelope detected data. Lateral and axial PSF profiles were taken from the centre of the point target. The lateral resolution was then assessed by measuring the width of the PSF at the −6 dB level and the axial resolution as the dimension of the PSF at the −6 dB level in the axial (depth) direction.

In addition, the performance of the proposed multitransducer system, in terms of image quality such a resolution, was described using a frequency domain or k-space representation. Axial-lateral RF PSFs were extracted from the beamformed data and the k-space representation was calculated using a 2-D Fourier transform. While the axial resolution is determined by the transmitted pulse length and the transmit aperture function, the lateral response of the system can be predicted by the convolution of the transmit and receive aperture functions [16].

Results

The 121 optimal parameter sets calculated for each of the transmit angles in the stationary experiment converged to the same results. The initial and optimal values obtained are summarized in Table I below.

TABLE I

INITIAL ESTIMATE AND OPTIMUM VALUES OF THE SYSTEM PARAMETERS

| Parameter | Initial value | Optimum value |
| --- | --- | --- |
| c | 1496 m/s | 1450.4 m/s |
| $Q_1$ | [8.54, 28.48] mm | [8.66, 28.16] mm |
| $Q_2$ | [3.78, 37.31] mm | [3.84, 36.87] mm |
| $Q_3$ | [−1.10, 45.05] mm | [−1.15, 45.41] mm |
| $Q_4$ | [−6.00, 54.07] mm | [−6.03, 53.94] mm |
| $Q_5$ | [−10.68, 62.00] mm | [−10.67, 62.12] mm |
| $\Phi_2$ | 55.33° | 56.73° |
| $O_2$ | [39.55, 22.83] mm | [38.80, 23.06] mm |

Figure 4:
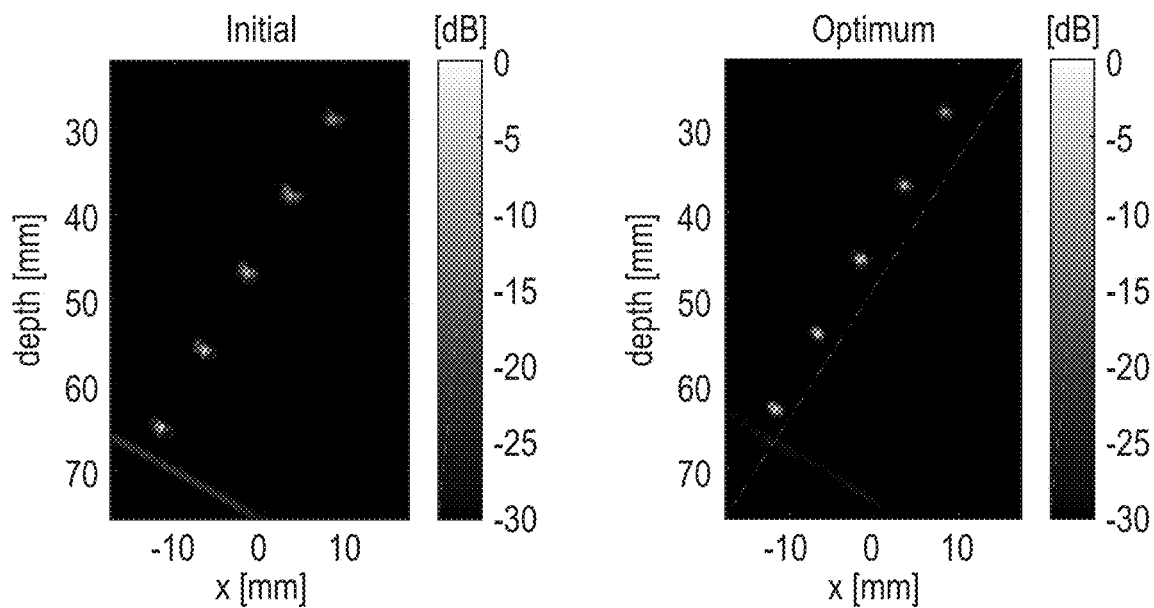
FIG. 4 shows graphically coherent multi-transducer images obtained using initial estimates of parameters and optimum values, the data corresponding to that shown in Table I.

FIG. 4 shows graphically coherent multi-transducer images obtained using initial estimates of parameters and optimum values, the data corresponding to that shown in Table I. It can be seen that a blurring effect on a PSF in an image obtained using initial estimates of positional parameters may be compensated after optimization methods are implemented.

The convergence illustrated in Table I and in FIG. 4 is also validated by results originating from the free-hand experiment. In this case, each transmit angle was optimized over total acquisition time. After calculating an initial estimate of positional parameters of a first transmitted PW, each subsequent optimization was initialized with the optimum value of the previous transmission event.

Figure 5:
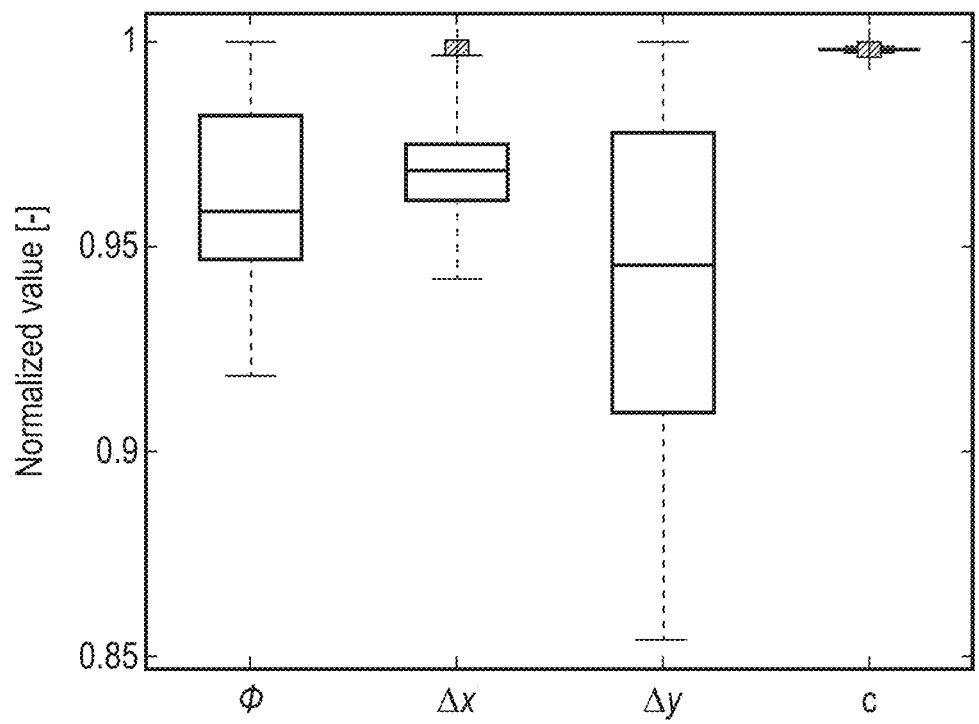
FIG. 5 is a box-plot of a normalized value of optimal parameters which define a rigid-body transformation between coordinate systems and the speed of sound over the duration of an experiment.

FIG. 5 is a box-plot of a normalized value of optimal parameters which define a rigid-body transformation between coordinate systems and the speed of sound over the duration of the experiment. As could be predicted, rotation and translation parameters present the higher value range, whilst the speed of sound in the medium can be considered substantially constant. The averaged value of the optimal speed of sound over the acquisition time was 1466.00 m/s and the standard deviation 0.66 m/s.

Figure 6:
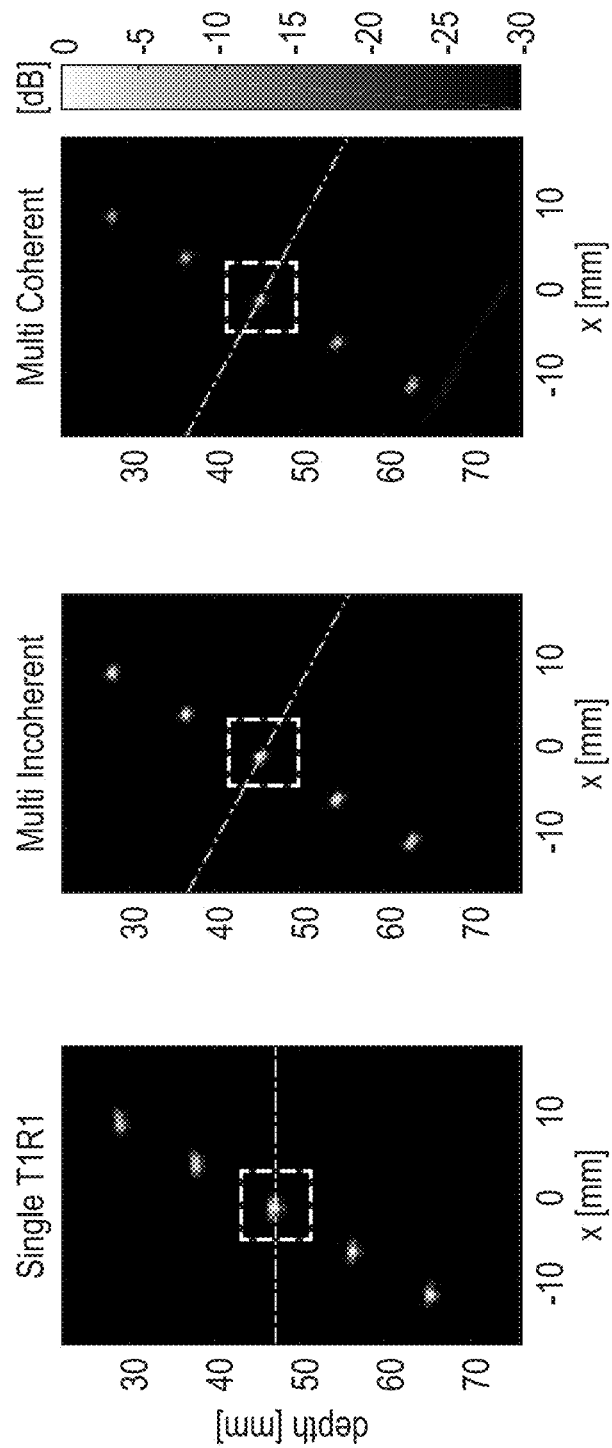
FIG. 6 shows images of a wire phantom obtained using a single transducer incoherently combined collected data and coherently combined collected data from two ultrasound transducers.

FIG. 6 shows images of a wire phantom obtained using a single transducer ($T_1R_1$) incoherently combined collected data (envelope detected images $T_1R_1$, $T_2R_2$) and coherently combined collected data ($T_1R_1$, $T_1R_2$, $T_2R_1$, $T_2R_2$) from two ultrasound transducers.

Comparison of the resulting images from a single transducer and those from a multitransducer method, it can be seen that the reconstructed images of the wire targets were clearly improved.

Figure 7:
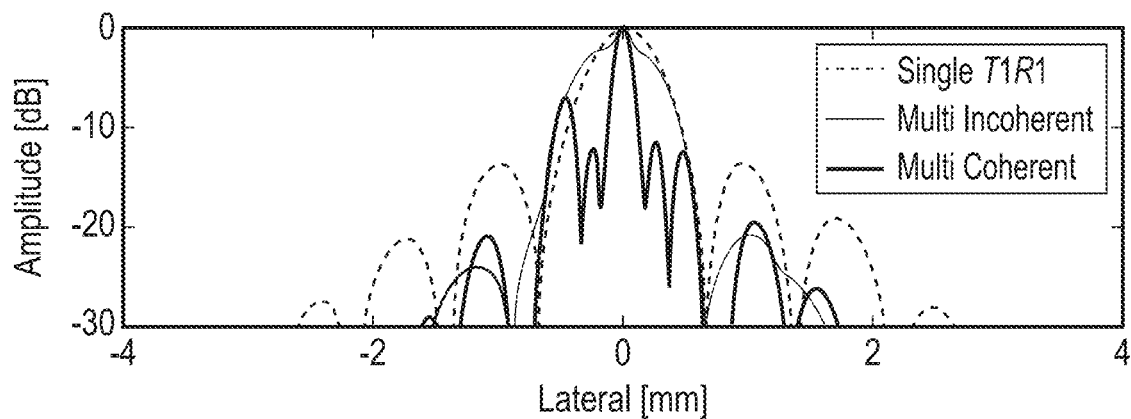
FIGS. 7 and 8 show a corresponding transverse cut of PSF at a scatterer depth indicated by FIG. 6.
Figure 8:
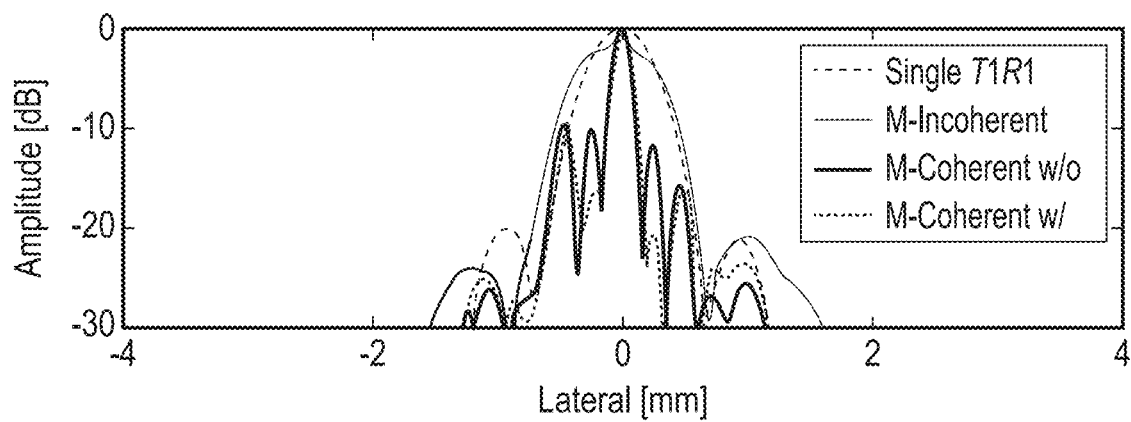

The PSFs of the three images can be compared. FIGS. 7 and 8 show a corresponding transverse cut of PSF at a scatterer depth indicated by FIG. 6 for each of the images, using a single PW at 0° and compounding 121 PW over a total angle range of 60°, respectively.

To analyse the multi-transducer method, a world coordinate system that leads to the best resolution and more conventional PSF shape is used. This coordinate system is defined by rotating the local coordinate system of transducer $T_1$ by the bisector angle between the two transducers. In this coordinate system, the best possible resolution is aligned with the x-axis. The incoherent multitransducer results show benefit from the optimization, since the optimum parameters were used to incoherently compound enveloped-detected sub-images $T_1R_1$ and $T_2R_2$. The effect of apodization in the multi-coherent PSF, accentuating the low lateral frequencies, was analysed in the PSF generated compounding 121 PW over a total angle range of 60°. The performance of all them is summarized in Table II.

TABLE II

IMAGING PERFORMANCE FOR THE DIFFERENT METHODS

|  | Axial resolution [mm] | Lateral Resolution [mm] | $1^{st}$ sidelobe [dB] | $2^{nd}$ sidelobe [dB] |
|---|---|---|---|---|
| PW Conventional | 0.9445 | 0.6674 | −14.96 | −20.79 |
| Multi Incoherent | 0.9474 | 0.7837 | −20.87 | — |
| Multi Coherent | 0.8109 | 0.1817 | −11.46 | −7.01 |
| PW Conventional (121 Angles) | 0.9002 | 0.6546 | −20.22 | — |
| Multi Coherent w/o (121 angles) | 0.8246 | 0.1911 | −9.94 | −9.64 |
| Multi Coherent w/ (121 angles) | 0.8391 | 0.2278 | −20.73 | −9.45 |

It can be seen that the coherent multi-transducer acquisition results in best lateral resolution, and worst lateral resolution corresponds to an incoherent image generated by combining the independent images acquired by both transducers.

Large differences are observed in the behaviour of the side lobes, which are higher in the coherent multi-transducer method. When a single PW is used, the biggest difference is between the second side lobes, being raised by 13 dB for the coherent multi-transducer method compared to the conventional single transducer method, while difference of the first side lobes is 3.5 dB. This suggests that whilst significant image improvements can be achieved, the image may suffer from the effects of side lobes. Apodization results in a significant reduction of the first side lobe and resolution improvement of 65% compared to a conventional image acquired by a single transducer.

Figure 9:
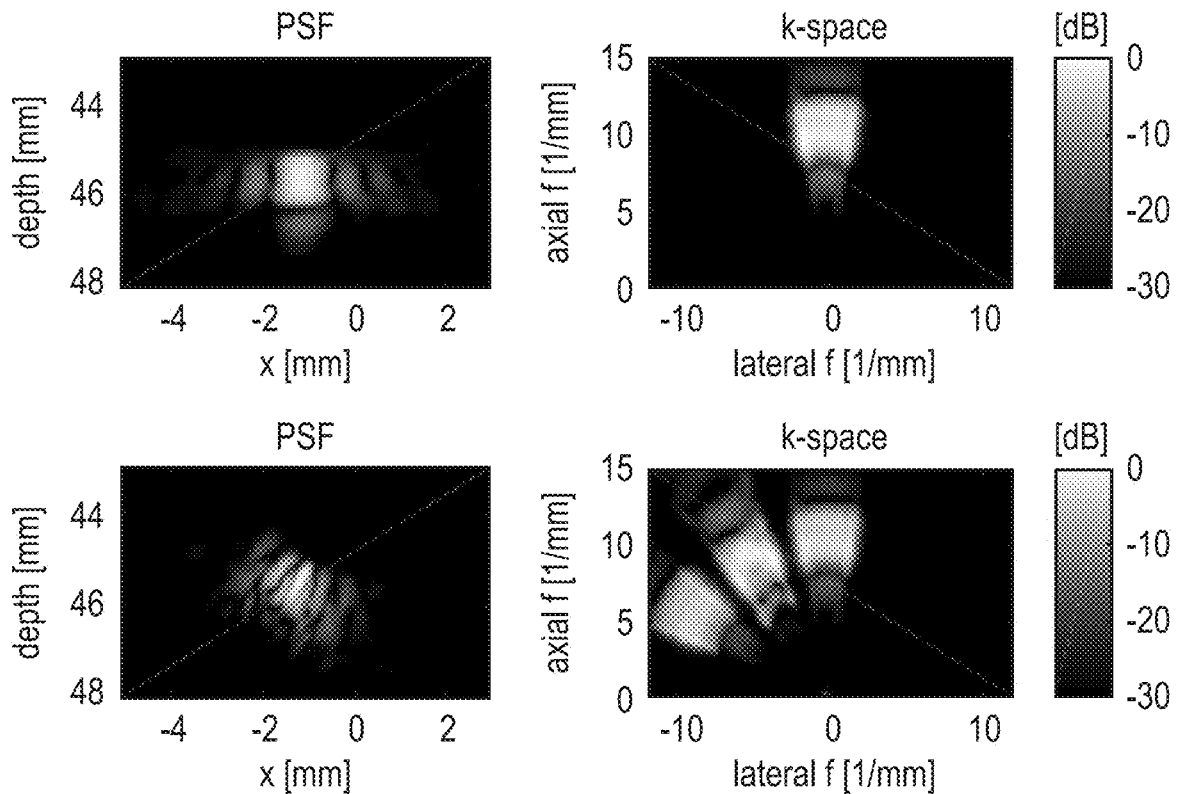
FIG. 9 shows a comparison of envelope-detected PSFs and k-space representation obtained using a single transducer and a coherent multi-transducer.

FIG. 9 shows a comparison of envelope-detected PSFs and k-space representation obtained using a single transducer and a coherent multi-transducer. The PSFs obtained using a single transducer ($T_1R_1$) and coherently compounding the images acquired by both transducers were analysed in the k-space representation. FIG. 9 shows the corresponding results using a single PW at 0°. Images are represented in the local coordinate system of transducer 1. An important consequence of the linear system is that the superposition principle can be applied. As expected, the total k-space representation shows an extended lateral region which corresponds to the sum of the four individual k spaces that form an image in the coherent multi-transducer method.

It will be appreciated that since both transducers are identical but have different spatial locations, they exhibit the same k-space response (identical transmit and receive aperture functions) but in different spatial locations. The discontinuity in the aperture of the system, given by the separation between the transducers, leads to gaps in the spatial frequency space. The discontinuity can be filled compounding PW over an angle range similar to the angle defined by the two transducers.

Figure 10:
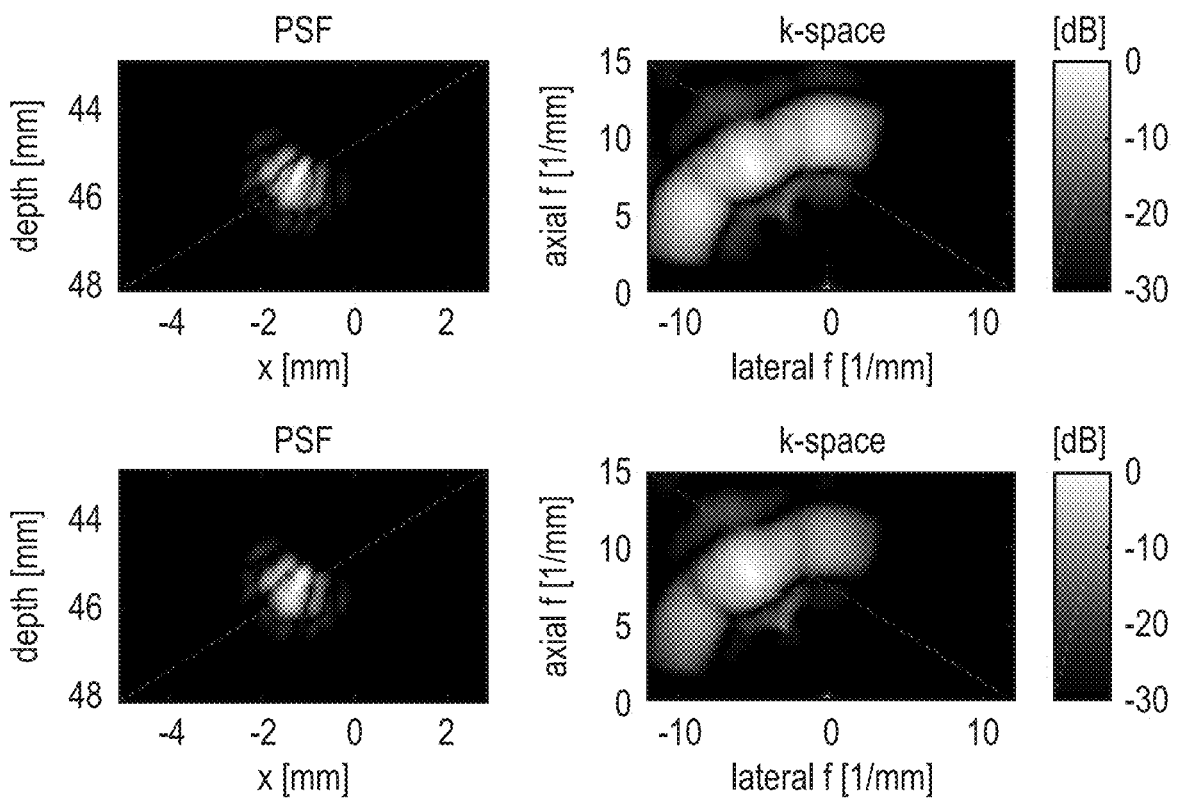
FIG. 10 illustrates envelope-detected PSFs and k-space representations of a multitransducer ultrasound method, compounding 121 plane waves covering a total angle range of 60°, without and with apodization.

FIG. 10 illustrates envelope-detected PSFs and k-space representations of a multitransducer ultrasound method, compounding 121 plane waves covering a total angle range of 60°, without and with apodization. In particular, FIG. 10 shows the resulting PSF after compounding 121 angles with a separation of 0.5°, which define a total sector of 60°, and the corresponding continuous k-space. The topography of the continuous k-space can be re-shaped by weighting data from the different images which are combined to form a final image. A more conventional transfer function, displaying reduced side lobes can be created accentuating the low lateral spatial frequencies, which are mostly defined by the sub-images $T_1R_2$ and $T_2R_1$. FIG. 10 shows a PSF and its corresponding k-space representation generated weighting the sub-images $T_1R_1$, $T_1R_2$, $T_2R_1$ and $T_2R_2$ with the vector [1; 2; 2; 1].

Discussion

The study described introduces a new synchronized multi-transducer ultrasound system and method which is capable of significantly outperforming conventional PW ultrasound imaging by coherently adding all individual images acquired by different transducers. In addition to an extended FoV that the use of multiple transducers allows for, improvements in resolution have been experimentally shown.

Furthermore, a final image formed from a coherent combination of sub-images may present different characteristics to those shown in the individual images. For example, a final image may have areas with optimal performance in a common FoV of multiple transducers, and its quality may deteriorate outside this region where the number of transducers with a shared FoV decreases. The worst regions of a final image will typically be defined by the performance of individual images and correspond to the parts of the combined "final" image with no overlapping FoV.

Different transmit beam profiles (such diverging waves) may increase the overlapped FoV and extend the high-resolution areas of a final image.

The significant differences between the k-space representations for the single and the multi-transducer methods shown in the Figures further explain differences in imaging performance. The more extended k-space representation, the higher resolution [17].

The appearance of the total response of a multi-transducer system can be explained using the rotation and translation properties of the 2-D Fourier transform. This total extent determines the highest spatial frequencies present in the image and therefore dictates resolution. The relative amplitudes of the spatial frequencies present, i.e. the topography of k-space, determine the texture of imaged targets. Weighting the data from the different transducers can reshape the k-space, accentuating certain spatial frequencies and allow for creation of a more conventional response of a system.

The presence of uniformly spaced unfilled areas in a system's k-space response may indicate the presence of grating lobes in the system's spatial impulse response [16]. A sparse array (such as the two-transducer system described above) creates gaps in k-space response. If a k-space has negligible gaps, the k-space magnitude response becomes smooth and continuous over a finite region. This is motivation to find and use a good spatial distribution for transducers in a system and suggests that while it may be beneficial to compound PW at different angles, it may not always be necessary in order to produce an improved image.

Wavefront aberration caused by an inhomogeneous medium can limit the quality of ultrasound images and is one significant barrier to achieving diffraction-limited resolution with large aperture transducers [18]. The method and apparatus described above have been tested in relation to a homogeneous medium, with the speed of sound constant along the propagation path. However, since the speed of sound is a parameter which may be optimised, the method described can be adapted to apply to non-homogeneous media in which the speed of sound varies in space. In this case, for example, the medium could be modelled by piecewise continuous layers. The optimization method could be applied in a recursive manner, dividing FoV into appropriate sub areas with different speeds of sound. More accurate speed of sound estimation may allow for improved beamforming and allow for higher order phase aberration correction. Furthermore, speed of sound maps are of great interest in tissue characterization [19], [20].

To successfully improve the PSF, the multitransducer method described above requires coherent alignment of the backscattered echoes from multiple transmit and receive positions. This requirement is achieved by a precise knowledge of all transducer positions, which in practice is not possible to achieve by manual measurements or using electromagnetic or optical trackers [21]. The method described above allows for precise and robust transducer location based upon spatial coherence of backscattered echoes coming from the same scatter and being received by the same transducer. The precise location of the transducers required for coherent image creation is calculated by optimizing spatial coherence. The use of gradient-descent methods requires an initial estimate of the parameters close enough to the global maximum of the cost function. The distance between maxima, which corresponds to the pulse length, dictates this tolerance. For the experimental configuration described above, this is approximately 1.5 μs (equivalent to 2.19 mm). This tolerance value can be achieved by imaging registration [14]. In practice, in a free-hand situation, and assuming that at some initial instant the registration is accurate, the initial guess can be ensured if the transducers move relatively little in the time between two transmissions. The method has been validated in a free-hand demonstration.

It will be appreciated that the experimental set up and associated method described above method is limited in that it assumes all transducers are located on the same plane, i.e. they share the same imaging plane. An alignment procedure before imaging acquisition has been performed to obtain the images shown in the Figures. The use of a 3-D matrix array allows those limitations to be overcome and can be used to build up higher-resolution volumes than current ultrasound transducer aperture sizes allow. It will also be appreciated that for convergence of the optimization algorithm described to a unique solution, N point scatterers, (same as number of transducers), may be needed in the common FoV. In reality, a plurality of notable scatterers within a medium are likely, so the limitation is not significant. Whilst the method has been validated for point scatterers, different scatterers may require a different approach.

Different transmit and receive paths experience unique clutter effects [22], generating spatially incoherent noise and PSF distortions that can form the basis for further work.

In conventional PW imaging, frame rate is limited by travel and attenuation times, which depend on the speed of sound and the attenuation coefficient. For the experimental setup described above, the minimum time between 2 isonifications is around 94 μs. Hence the maximum frame rate is limited to 10.7 kHz, which is reduced when different compounding angles are used. In the case of a multi-transducer method, the frame rate is reduced by the number of transducers as $F_{max}/N$.

Figure 11:
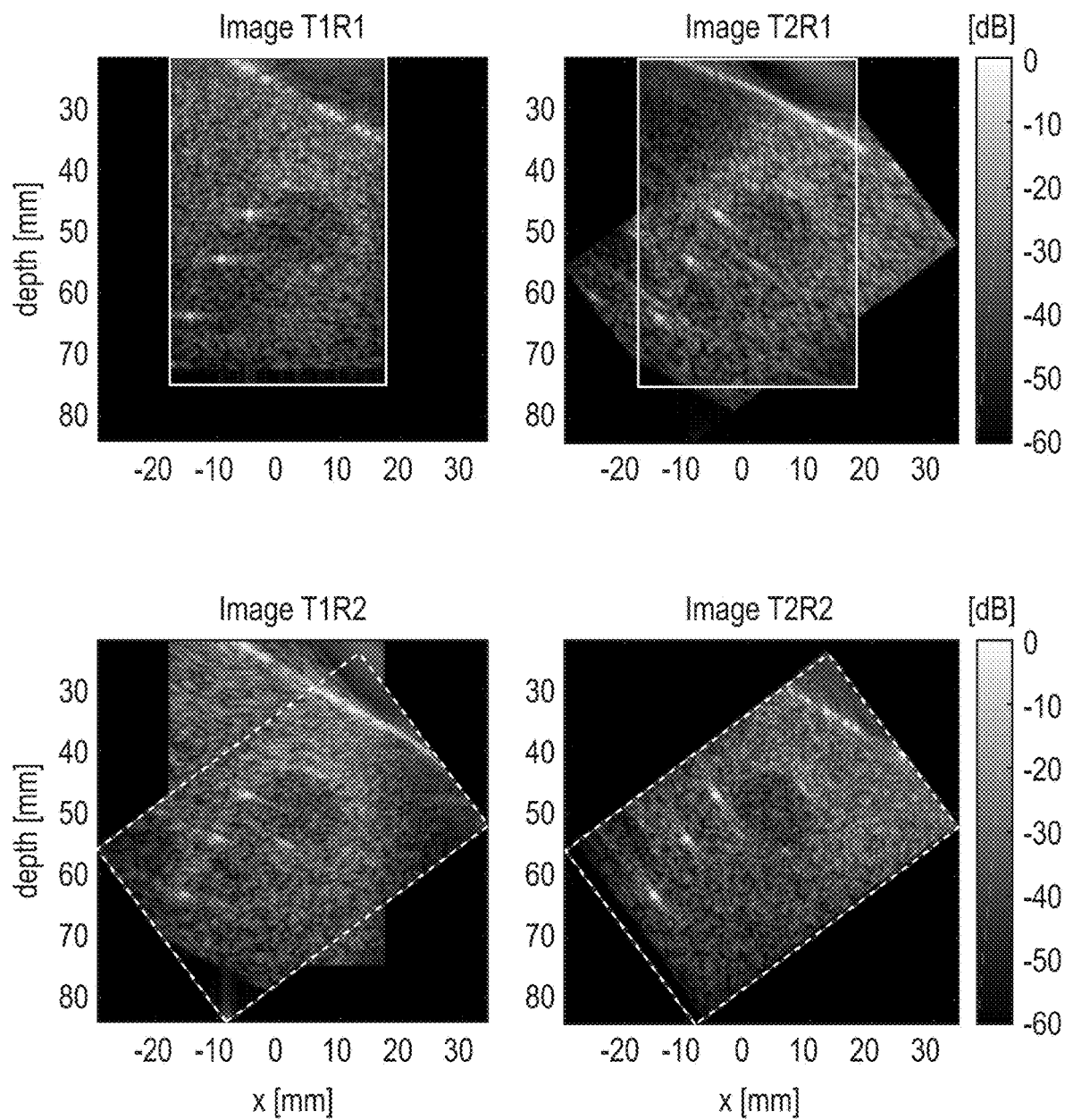
FIG. 11 shows a set of individual sub-images forming a final "multi coherent" image.

FIG. 11 shows a set of individual sub-images forming a final "multi coherent" image. These were obtained by individually beamforming the 4 RF datasets acquired from one complete sequence, i.e. transmitting a PW at 0° with probe T1 and simultaneously receiving with both probes ($T_1R_1$, $T_1R_2$) and repeating the transmission with probe $T_2$ ($T_2R_1$, $T_2R_2$). The optimum parameters used to reconstruct the images are $\varphi_2=53.05°; O_2=[41.10, 25.00]$ mm, c=1437:3 m/s. Lines indicate the field of view of transducer $T_1$ (upright) and $T_2$ (slanted).

Figure 12:
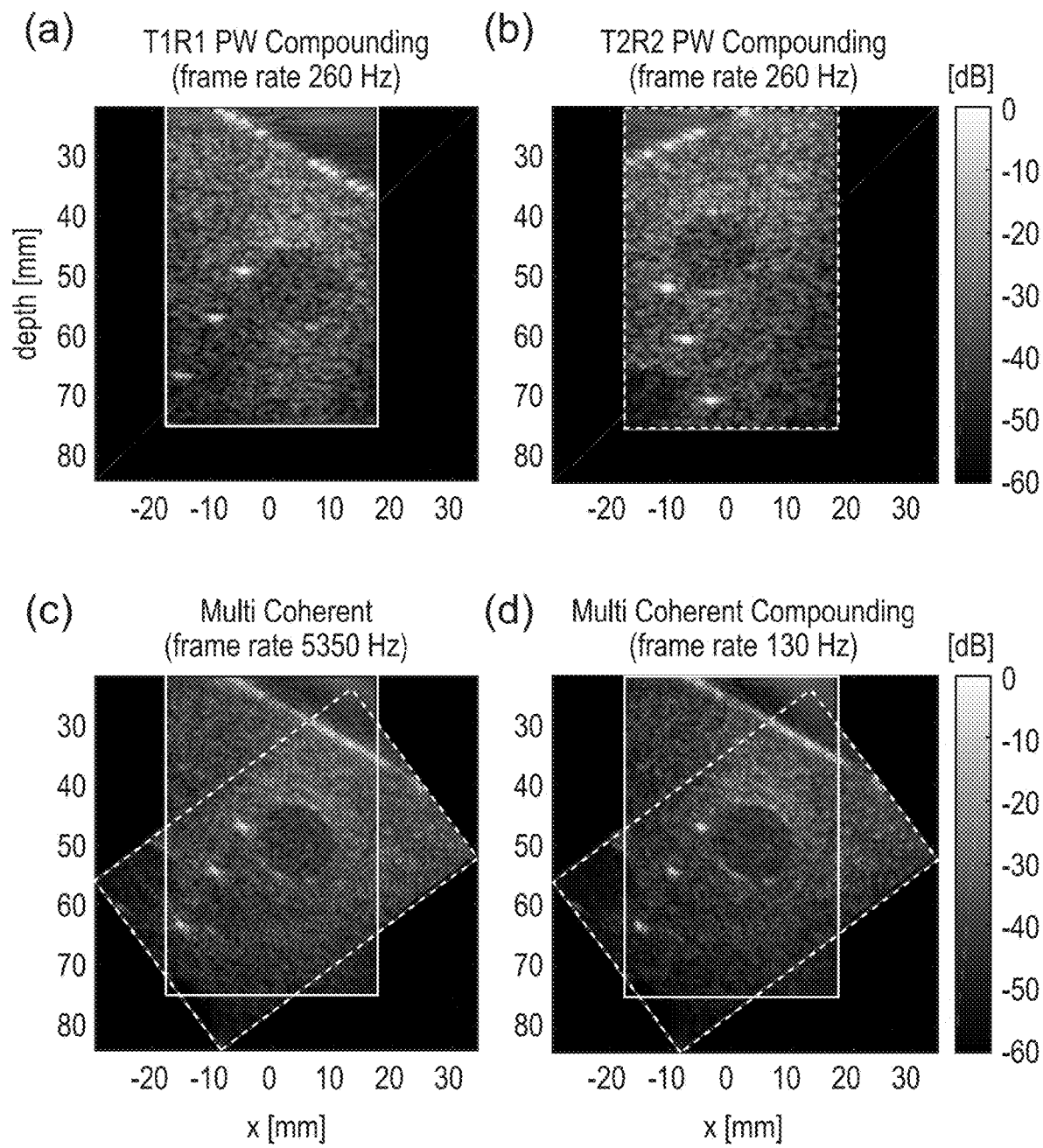
FIG. 12 shows experimental images of a contrast phantom obtained by different methods.

FIG. 12 shows experimental images of a contrast phantom obtained by different methods. FIG. 12(a) shows coherent plane wave compounding 41 PW with transducer $T_1$; FIG. 12(b) shows coherent plane wave compounding 41 PW with transducer $T_2$; FIG. 12(c) shows coherent multi transducer method with transmission of a single PW at 0° from each transducer; FIG. 12(d) shows coherent multi transducer method with additional compounding and each transducer emitting 41 PW. The optimum parameters used to reconstruct the multi-coherent images are $\varphi_2=53:05°; O_2=[41.10; 25.00]$ mm, c=1437:3 m/s. Lines indicate the field of view of transducer $T_1$ (upright) and $T_2$ (slanted).

The results obtained from the anechoic lesion phantom are presented in FIGS. 11 and 12, where the field of view (FoV) of each transducer is indicated by upright and slanted lines ($T_1$ and $T_2$ respectively). FIG. 11 shows the individual sub-images that form the final multi coherent image and that are obtained through beamforming the 4 RF datasets acquired in a single cycle of the imaging process, i.e. transmitting a PW at 0° with probe $T_1$ and simultaneously receiving with both probes ($T_1R_1, T_1R_2$) and repeating the transmission with probe $T_2$ ($T_2R_1, T_2R_2$). Reconstruction of these sub-images is possible after finding, through optimization, relative positions of the probes. A direct result of the combination of these 4 sub images is the extended FoV of the multi coherent image. FIG. 12(c) shows a multi coherent image obtained by coherently compounding 4 sub-images. It can be seen that, as predicted by a k-space representation, any overlapping regions in the sub-images will contribute to improved resolution in the final multi coherent image because of the effective enlarged aperture created.

Images acquired using coherent PW compounding with a single transducer ($T_1R_1$ and $T_2R_2$, compounding 41 PW angles) and coherently compounding the RF data acquired by both transducers (using equation (6)) transmitting each one a single PW at 0° and transmitting each one 41 PW are compared in FIG. 12.

TABLE II

IMAGING PERFORMANCE FOR THE DIFFERENT METHODS ASSESSED USING THE CONTRAST PHANTOM

| | Lateral resolution [mm] | Contrast [dB] | CNR [-] | Frame rate [Hz] |
|---|---|---|---|---|
| Single $T_1R_1$ (1 PW at 0°) | 2.633 | −6.708 | 0.702 | 10700 |
| Single $T_1R_1$ Compounding (41 PW, sector 20°) | 1.555 | −8.260 | 0.795 | 260 |

TABLE II-continued

IMAGING PERFORMANCE FOR THE DIFFERENT
METHODS ASSESSED USING THE CONTRAST PHANTOM

|  | Lateral resolution [mm] | Contrast [dB] | CNR [-] | Frame rate [Hz] |
|---|---|---|---|---|
| Multi Coherent (1 PW at 0°) | 0.713 | −7.251 | 0.721 | 5350 |
| Multi Coherent Compounding (41 PW per array, sector 20°) | 0.693 | −8.608 | 0.793 | 130 |

Table II above shows the corresponding imaging metrics in terms of lateral resolution, contrast, CNR and frame rate. To reconstruct the coherent multi-transducer images, the initial estimate of parameters was chosen as described above and 3 strong scatterers generated by nylon wires were used in the optimization. It can be seen that, in general, the multi coherent image has better defined edges, making the border easier to delineate than in an image obtained by a single transducer. The reconstructed images of the wire targets are clearly improved, the speckle size is reduced and the anechoic region is easily identifiable from the phantom background. Resolution significantly improved in the coherent multi-transducer method without frame rate sacrifice and at small expense of contrast. For single transducer, with coherent compounding, the lateral resolution, measured at the first target position is, 1.555 mm (measured at a frame rate of 260 Hz). Using multi-probe image (without additional compounding) the resolution improved to 0.713 mm (with an improved frame rate of 5350 Hz). In the single transducer case, a lesion is visible with a contrast of −8.26 dB and a CNR of 0.795, while both metrics are slightly reduced in the multitransducer coherent image (without additional compounding) to −7.251 dB and 0.721, respectively. Using compounding with 41 PW over each probe these improve to −8.608 dB and 0.793. These results suggest that target detectability is a function of both resolution and contrast.

Figure 13:
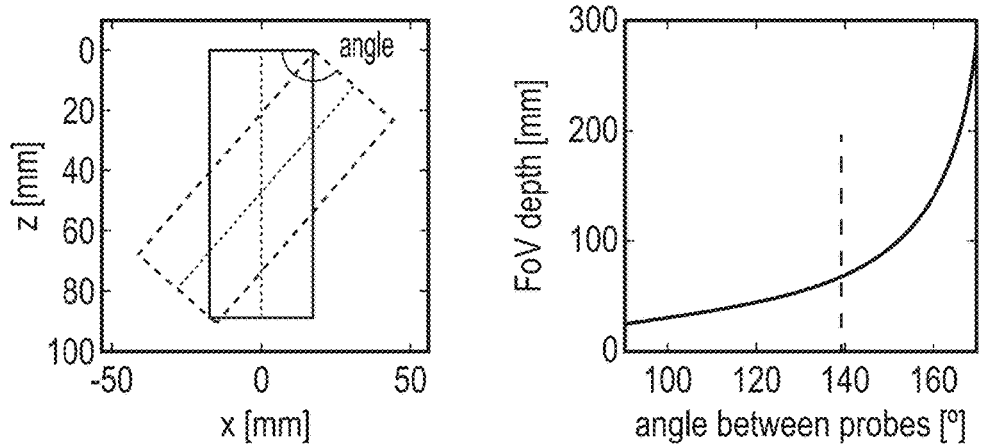
FIG. 13 is a schematic representation of a common field of view (FoV) of two probes T1 and T2.

The dependence of the imaging depth on the angle between both probes has also been investigated. FIG. 13 shows a spatial representation of the FoV of two linear arrays and the depth of the common FoV, measured at the intersection of the centre of both individual fields of view. The depth of common FoV as function of the angle between both probes when transmitting plane waves at 0° is described. It can be seen from FIG. 13 that imaging depth increases at larger angle between the probes.

Described arrangements introduce a coherent multi-transducer ultrasound system that significantly outperforms single transducer arrangements through coherent combination of signals acquired by different synchronized transducers that have a shared FoV. Although the experiments described were performed as a demonstration in 2-D using linear arrays, the framework proposed encompasses the 3rd spatial dimension. The use of matrix arrays capable of volumetric acquisitions may be used for a true 3-D demonstration. Since the multicoherent image is formed by 4 RF datasets that are acquired in two consecutive transmissions, it will be appreciated that tissue and/or probe motion do not break the coherence between consecutive acquisitions. To ensure this is the case, high frame rate acquisition is useful. Whilst described arrangements use plane waves, different transmit beam profiles such as diverging waves may increase the overlapped FoV, extending the final high-resolution image. Indeed, there is a complex interplay between FoV and resolution gain as probes are moved relative to one another.

In the method presented overlap of insonated regions allows relative probe positions to be determined. Any overlap in either transmit or receive sensitivity fields contributes to improved resolution because of the enlarged aperture of the combination of transducers. The final image achieves an extended FoV, but the resolution will only improve in regions of overlapping fields. This is best towards the centre where overlap includes transmission and reception for both individual probes. There is also an improvement (albeit lesser) in regions where the overlap is only on transmit or receive fields (see FIGS. 11 and 12). Thus, there are net benefits, but of different kinds, in different locations. In a similar way, this also will determine the imaging depth achieved by described methods. Whilst the relative position of the individual transducers and the angles of the transmitted plane waves determines depth of common FoV (see FIG. 12), an improvement of imaging sensitivity in deep regions is expected since the effective receive aperture is larger than in a single probe system.

Improvements in resolution are primarily determined by an effective extended aperture rather than compounding PW at different angles. Results show that in the coherent multi-transducer method there is a trade-off of between resolution and contrast [18]. While a large gap between the probes will result in an extended aperture which improves resolution, the contrast may be compromised due to the effects of sidelobes associated with creation of a discontinuous aperture. Further coherent compounding can be used to improve the contrast by reducing sidelobes. FIG. 12 illustrates that target detectability is determined by both resolution and contrast [29]. The differences between k-space representations for the single and the coherent multi-transducer methods further explain the differences in imaging performance; the more extended the k-space representation, the higher the resolution [30]. The relative amplitudes of the spatial frequencies present, i.e. the topography of k-space, determine the texture of imaged targets. Weighting the individual data from the different transducers can reshape the k-space, accentuating certain spatial frequencies and so can potentially create a more conventional response for the system. Moreover, the presence of uniformly spaced unfilled areas in a system's k-space response may indicate the presence of grating lobes in the system's spatial impulse response [28]. A sparse array may create gaps in the k-space response. Only with minimal separation between transducers the k-space magnitude response will become smooth and continuous over an extended region. This suggests that there is an interplay between the relative spatial positioning of the individual transducers and the angles of the transmitted plane waves; where either one or both of these can determine the resolution and contrast achievable in the final image [18].

Relative position data can be used to decide what range of PW angles to use and to change these in real time to adaptively change system performance. In real life applications, resolution and contrast will be influenced by a complex combination of probe separation and angle, aperture width, fired PW angle and imaging depth. It will be appreciated that different factors may determine the image performance of the system. Image enhancements related to increasing aperture size are well described [12]. Nevertheless, in clinical practice the aperture is limited because extending it often implies increasing system cost and complexity. Described implementations use conventional equipment and image-based calibration to extend the effective aperture size while increasing the received amount of RF data (data x N).

Estimated time for "first" initialization of a system in accordance with described arrangements is less than 1 minute, which is comparable to other calibration methods [31], [32]. Once the algorithm has been correctly initialized, the subsequent running times for the optimization can be significantly decreased. For example, in the free-hand experiment, where each optimization was initialized with the output from the previous acquisition, the optimization was up to 4 times faster than the first one.

Regarding to the amount of data, similar to 3-D and 4-D ultrafast imaging where the data is significantly large [33], in the proposed multi-transducer method computation may be a bottleneck for real time imaging. Graphical processing unit (GPU)-based platforms and high-speed buses are key to future implementation of these new imaging modes [34].

In addition to the system complexity, large-aperture arrays represent ergonomic operator problems and have limited flexibility to adapt to different applications. In described arrangements, an extended aperture is the result of adding multiple freely placed transducers together, which allows more flexibility. Small arrays are easy to couple to the skin and adapt to the body shape. Whilst use of multiple probes may increase the operational difficulty for an individual performing the scan, it is possible to manipulate multiple probes using a single, potentially adjustable, multiprobe holder that would allow the operator to hold multiple probes with only one hand while keeping directed to the same region of interest. Such a probe holder has been demonstrated as a potential device for incoherent combination of multiple images for extended FoV imaging [4].

Approaches and arrangements described may provide a different strategy in ultrasound according to which large assemblies of individual arrays may be operated coherently together. To successfully improve the PSF, multitransducer methods according to arrangements require coherent alignment of backscattered echoes from multiple transmit and receive positions. This can be achieved through precise knowledge of all transducer positions, which in practice is not achievable by manual measurements or using electromagnetic or optical trackers [35]. Approaches described provide methods for precise and robust transducer location by maximizing coherence of backscattered echoes arising from the same point scatterer and received by the same transducer using sequential transmissions from each of transducer of a system.

Equivalent to applications providing free-hand tracked ultrasound for image guide applications [31], [32], spatial calibration helps to guarantee performance of described multi-coherent ultrasound methods. It will be appreciated that use of gradient-descent methods requires an initial estimate of parameters close enough to a global maximum of a cost function, including the position of calibration targets. The distance between maxima, which depends on NCC and corresponds to the pulse length, dictates this tolerance. This is approximately 1.5 μs (equivalent to 2.19 mm) for the experimental configuration described above. This tolerance value can be realistically achieved through image registration [27]. In practice, in a free-hand situation, and assuming that at some initial instant the registration is accurate, this initial guess can be ensured if the transducers move relatively little in the time between two transmissions and share a common FoV. In PW imaging, the frame rate is only limited by the round-trip travel time, which depends on the speed of sound and the depth. For the experimental setup described, the minimum time between two insonifications is around 94 μs. Hence the maximum frame rate is limited to $F_{max}=10:7$ kHz, which in the case of the described multi transducer coherent method, is reduced by the number of probes as $F_{max}/N$. To guarantee free-hand performance of the described implementation of a multi transducer method, perfect coherent summation must be achieved over consecutive transmissions of the N transducers of the system. However, when the object under insonification moves between transmit events, this condition is no longer achieved. In other words, the free-hand performance is limited by the maximum velocity at which the probes move. Considering that coherence breaks for a velocity at which the observed displacement is larger than half a pulse wavelength per frame [26], the maximum velocity of the probes is $V_{max}=\lambda F_{max}/2N$, which in the example shown here is 1.33 m/s. This speed far exceeds the typical operator hand movements in a regular scanning session and hence, the coherent summation over two consecutive transmission is achieved. The method has been validated in a free-hand demonstration.

Wavefront aberration caused by inhomogeneous medium can significantly limit the quality of medical ultrasound images and is the major barrier to achieve diffraction-limited resolution with large aperture transducers [36]. The technique described in this work has been tested in a scattering medium, with the assumption of a constant speed of sound along the propagation path. However, since the speed of sound is a parameter in the optimization, the technique could be adapted for nonhomogeneous media where the speed of sound varies in space [18]. In this case, the medium could be modelled through piecewise continuous layers. The optimization method could be applied in a recursive way, dividing the FoV in sub areas with different speeds of sound. More accurate speed of sound estimation would improve beamforming and allow higher order phase aberration correction. It will be appreciated that "speed of sound" maps would be of great interest in tissue characterization [37], [38].

In addition, the use of multiple transducers allows multiple interrogations from different angles, which might give insight into the aberration problem and help to test new algorithms to remove the clutter.

The approach presented here has been formulated and validated for detectable and isolated point scatterers within the shared imaging region, which in practice may not be always possible. Whilst the theory has been presented in relation to point-like scatterers, approaches rely on a measure of coherence which may well be more tolerant, as indicated in the contrast phantom demonstrated in FIG. 12. This suggests that the method may work when there are identifiable prominent local features, and the concept of maximizing coherence of data received by each receiver array when insonated by different transmitters could allow wider usage. Indeed, an optimization based on spatial coherence might be more robust in the case where point targets are not available, due to the expected decorrelation of speckle with receiver location [39]—[41]. This may also lead to improvements in computational efficiency. Measures of spatial coherence have been used previously in applications such as phase aberration correction [42], flow measurements [43], and beamforming [44]. On the other hand, isolated point scatterers can be artificially generated by other techniques, for instance by inclusion of microbubble contrast agents [45].

Ultrasound super-resolution imaging recognises that spatially isolated individual bubbles can be considered as point scatterers in the acoustic field and accurately localized [47].

The feasibility of the coherent multi-transducer method in complex media, including a new approach mainly based on spatial coherence [20], and the potential use of microbubbles.

Arrangements described may provide a new coherent multi-transducer ultrasound imaging system and a robust method to accurately localize the multiple transducers. The subwavelength localization accuracy required to merge information from multiple probes is achieved by optimizing the coherence function of the backscattered echoes coming from the same point scatterer insonated by sequentially all transducers and received by the same one, without the use of an external tracking device.

The theory described has application with a multiplicity of 2-D arrays placed in 3-D and the method was experimentally validated in a 2-D framework using a pair of linear array and ultrasound phantoms. The improvements in imaging quality have been shown. Overall the performance of the multi-transducer approach is better than PW imaging with one single linear array. Results suggest that the coherent multitransducer imaging has the potential to improve ultrasound image quality in a wide range of scenarios.

As described above, a coherent multi-transducer ultrasound imaging system (CMTUS) enables an extended effective aperture (super-aperture) through coherent combination of multiple transducers. As described above, an improved quality image can be obtained by coherently combining the radio frequency (RF) data acquired by multiple synchronized transducers that take turns to transmit plane waves (PW) into a common FoV). In such a coherent multi-transducer ultrasound (CMTUS) method, optimal beamforming parameters, which include the transducer locations and an average speed of sound in a medium under study, can be deduced by maximizing coherence of received RF data by cross-correlation techniques. As a result, a discontinuous large effective aperture (super aperture) is created, significantly improving imaging resolution. While the use of multiple arrays to create a large aperture instead of using a single big array may be more flexible for different situations such as typical intercostal imaging applications where the acoustic windows are narrow, the discontinuities dictated by the spatial separation between the multiple transducers may determine the global performance of the CMTUS method. It will be appreciated that as a consequence of the discontinuous aperture there is a trade-off between resolution and contrast.

Arrangements recognise that since average speed of sound in a medium under study is optimized by the CMTUS method, an improvement in the beam formation with some higher order phase aberration correction is expected.

Inhomogeneous Media

A k-Wave Matlab toolbox was used to simulate the non-linear wave propagation through an inhomogeneous medium (Treeby and Cox, 2010; Treeby et al., 2012). A CMTUS system formed by two identical linear arrays, similar to the ones experimentally available, was simulated as follows:

Each of the arrays had a central frequency of 3 MHz and 144 active elements in both transmit and receive, with element pitch of 240 μm and kerf of 40 μm. For plane waves the modelled transducer had an axial focus of infinity with all 144 elements firing simultaneously. The apodisation across the transducer was modelled by applying a Hanning filter across the transducer width. Table IV summarizes the simulation parameters that define each of the linear arrays.

TABLE IV

| Parameter | Value |
|---|---|
| Number of elements | 144 |
| Pitch | 240 μm |
| Kerf | 40 μm |
| Central frequency | 3 MHz |
| Transmit pulse cycles | 3 |
| Sampling frequency (downsampled) | 30.8 MHz |

A simulation was performed for each transmit event, i.e. each plane wave at a certain angle. In total 7 transmit simulations per linear array were performed to produce a plane wave data set, which covers a total sector angle of 30° (from −15° to 15°, 5° step). In the case of CMTUS this results in 14 transmit events in total (7 plane waves per array). This plane wave sequence was chosen to match in resolution a focused system with F-number 1.9, decimating the required number of angles by a factor of 6 to optimize the simulation time without affecting resolution. The spatial grid was fixed at 40 μm (six grid points per wavelength) with a time step corresponding to a Courant-Friedrichs-Lewy (CFL) condition of 0.05 relative to a propagation speed of 1540 m/s. Received signals were downsampled at 30.8 MHz. Channel noise was introduced to the RF simulated data as Gaussian noise with a SNR of 35 dB at 50 mm imaging depth.

The ultrasound pulses were propagated through heterogeneous scattering media using tissue maps (speed of sound, density, attenuation and nonlinearity). A medium defined only with the properties of general soft tissue was used as control case. To model the scattering properties observed in vivo, sub-resolution scatterers were added to the tissue maps. A total of 15 scatterers of 40 μm diameter, with random spatial position and amplitude (defined by a 5% difference in speed of sound and density from the surrounding medium), were added per resolution cell, in order to fully develop speckle. Three point-like targets and an anechoic lesion were included in the media to allow the measurement of the basis metrics for comparing the imaging quality for different scenarios. A circular anechoic lesion of 12 mm diameter located at the centre of the aperture of both arrays (common FoV), was modelled as a region without scatterers. The point-like targets were simulated as circles of 0.2 mm diameter with a 25% difference in speed of sound and density with the surrounding tissue to generate appreciable reflection. The same realization of scatterers was superimposed on all maps and through the different simulations to keep the speckle pattern in the CMTUS system, so any changes in the quality imaging metrics are due to changes in the overlying tissues, the imaging depth and the acoustical field.

The k-Wave Matlab toolbox uses a Fourier co-location method to compute spatial derivatives and numerically solve the governing model equations, which requires discretisation of the simulation domain into an orthogonal grid. Consequently, continuously defined acoustic sources and media need to be sampled on this computational grid, introducing staircasing errors when sources do not exactly align with the simulation grid. To minimize these staircasing errors, the transmit array was always aligned to the computational grid, i.e. simulations were performed in the local coordinate system of the transmit array. This implies that to simulate a sequence in which the array T2 transmits, the propagation medium, including the sub-resolution scatterers, was converted into the local coordinate system of probe T2 using the same transformation matrix that defines the relative position of both transducers in space. A sample tissue map with the transducers, point-like targets and anechoic lesion locations, represented in both local coordinate systems, is shown in FIG. 14.

Figure 14A:
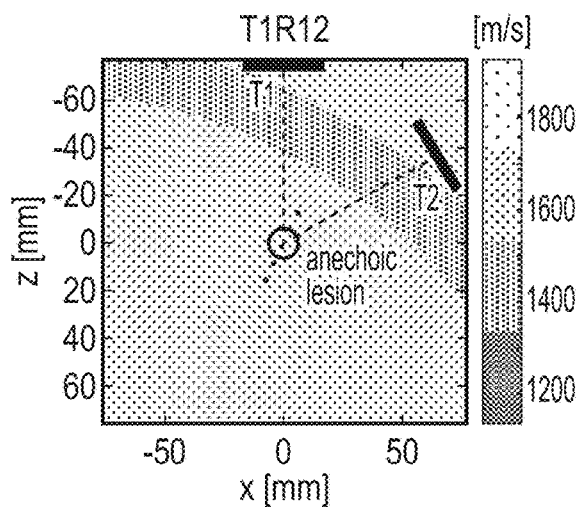
FIG. 14 illustrates an example of a speed of sound map of a propagation medium with a muscle layer of 8 mm thickness and a fat layer of 25 mm.
Figure 14B:
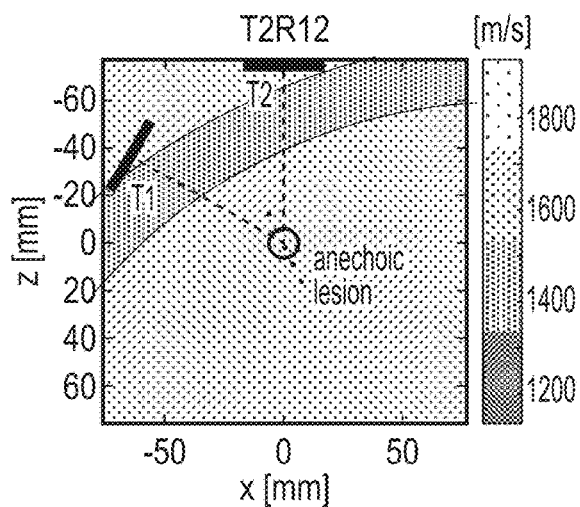

FIG. 14 illustrates an example of a speed of sound map of a propagation medium with a muscle layer of 8 mm thickness and a fat layer of 25 mm. Locations of ultrasound probes, point-like targets and anechoic lesion are shown. FIG. 14 (a) shows the medium expressed in the local coordinate system of the array T1 and used to simulate the RF data T1R12, i.e. when the array $T_i$ transmits. FIG. 14 (b) shows the medium expressed in the local coordinate system of the array $T_2$ and used to simulate the RF data T2R12, i.e. when the array $T_2$ transmits. In this example, the angle between the probes that defines their position in space is 60° and the corresponding imaging depth 75 mm.

CMTUS Discontinuous Effective Aperture

It is demonstrated above that the discontinuous effective aperture obtained by CMTUS determines the quality of the resulting image. To investigate the effects of the discontinuous aperture, determined by the relative location of the CMTUS arrays in space, different CMTUS systems with the arrays located at different spatial locations were modelled. Simulations were performed in the same control medium, where only soft tissue material was considered. To modify the relative location of the probes while keeping the imaging depth (fixed at 75 mm), the angle between the arrays was changed. The array T1 was always positioned at the centre of the x-axis of the simulation grid while the array $T_2$ was rotated around the centre of the propagation medium. Then, different cases of CMTUS with two arrays located at different angles, from 30° to 75° in steps of 15°, were simulated.

Figure 15:
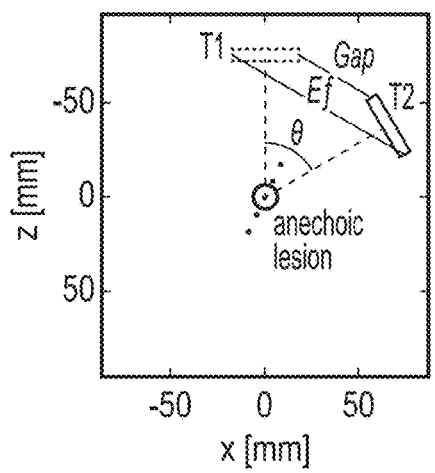
FIG. 15 is a schematic representation of spatial location of two linear arrays.

FIG. 15 shows a schematic representation of the probes in space, where the different spatial parameters (angle between probes, θ, and gap, Gap, in the resulting effective aperture, Ef) are labelled. Note that, at larger angles, both the effective aperture of the system defined by both probes and the gap between them increase. The relationships between probe position, and the resulting effective aperture and gap are shown in FIG. 15.

CMTUS Image Penetration

Figure 16:
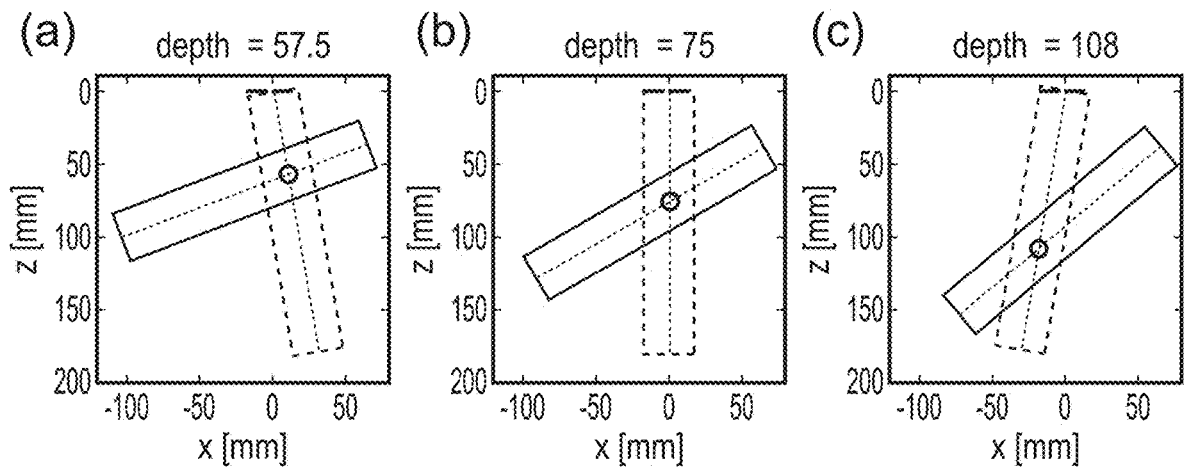
FIG. 16 is a schematic representation of spatial location of two linear arrays and their field of view at different imaging depths.

The image penetration of CMTUS was investigated by changing the local orientation of the arrays and using the same control propagation medium (only soft tissue). For a given effective aperture (fixed gap), each probe was rotated around its centre the same angle but in the opposite direction. In that way, a certain given rotation, for example negative in T1 and positive in T2 will result in a deeper common FoV, and the opposite for the counter-rotation. FIG. 16 shows the imaging depth dependence on the transducer orientation (defined by the position of the common FoV of both arrays). Using this scheme, four different imaging depths were simulated: 57.5 mm, 75 mm, 108 and 132 mm.

FIG. 16 shows a schematic representation of the spatial location of the two linear arrays, T1 and T2, and their field of view at different imaging depths. The imaging depth is obtained steering the linear arrays the same angle but in opposite directions. Three different cases are shown: (a) 57.5 mm imaging depth; (b) 75 mm imaging depth; and (c) 108 imaging depth. The circle indicates the centre of the common field of view, which defines the imaging depth in CMTUS.

CMTUS Through Aberrating Media

To investigate the effect of aberrating inhomogeneities in the medium, three different kinds of tissue were defined in the propagation media (general soft tissue, fat and muscle). The imaging depth was set to 75 mm with a configuration of the arrays in space that defines an effective aperture of 104.7 mm with 45.3 mm gap. The acoustic properties assigned to each tissue type were chosen from the literature and are listed below:

| Tissue type | Speed of Sound [m/s] | Density [kg/m³] | Attenuation [dB/MHz/cm] | Nonlinearity B/A |
|---|---|---|---|---|
| Soft tissue | 1540 | 1000 | 0.75 | 6 |
| Fat | 1478 | 950 | 0.63 | 10 |
| Muscle | 1547 | 1050 | 0.15 | 7.4 |

A medium defined only with the soft tissue properties was used as control case. Then, clutter effects were analysed by using heterogenous media in which two layers with the acoustic properties of muscle and fat were introduced into the control case medium. In the different studied cases, the thickness of the muscle layer was set to 8 mm while fat ranged from 5 to 35 mm thickness. FIG. 14 shows an example of the propagation medium with a muscle layer of 8 mm and a fat layer of 25 mm.

In-Vitro Experiments

A sequence similar to the one used in simulations was used to image a phantom. The imaging system consisted of two 256-channel Ultrasound Advanced Open Platform (ULA-OP 256) systems (MSD Lab, University of Florence, Italy). The systems were synchronized, i.e. with the same trigger and sampling times in both transmit and receive mode. Each ULAOP 256 system was used to drive an ultrasonic linear array made of 144 piezoelectric elements with a 6 dB bandwidth ranging from 2 MHz to 7.5 MHz (imaging transducer LA332, Esaote, Firenze, Italy). The two probes were mounted on xyz translation and rotation stage (Thorlabs, USA) and were carefully aligned in the same elevational plane (y=0). For each probe in an alternating sequence, i.e. only one probe transmits at each time while both probes receive, 7 PW, covering a total sector angle of 30° (from −15° to 15°, 5° step), were transmitted at 3 MHz and pulse repetition frequency (PRF) of 1 kHz. RF data backscattered up to 135 mm deep were acquired at a sampling frequency of 19.5 MHz. No apodization was applied either on transmission or reception. A subset of the simulated results was experimentally validated in-vitro. A phantom custom made with three point-like targets and ananaechoic region, was imaged with the imaging system and pulse sequences described below. The averaged speed of sound of the phantom was 1450 m/s. The phantom was immersed in a water tank to guarantee good acoustic coupling. To induce aberration, a layer of paraffin wax of 20 mm thickness was placed between the probes and the phantom. The measured speed of sound of paraffin wax was 1300 m/s.

The control experiment was performed first without the paraffin wax sample present. After the control scan, the paraffin wax sample was positioned over the phantom without movement of the phantom or tank. Then, the target was scanned as before. The paraffin wax sample was positioned to sit immediately over the phantom, coupled to the transducers by water. A final control scan was performed to verify registration of the phantom, tank and transducers, after the paraffin wax sample was scanned and removed.

Data Processing

The RF data, both simulated and experimentally acquired, were processed in different combinations to study image quality. For a single probe system, beamforming of RF data was performed using the conventional delay-and-sum method for coherent plane wave compounding. The multi-transducer beamforming was performed as described above.

For each simulated case, the optimum beamforming parameters, calculated by maximizing the cross-correlation of backscattered signals from common targets acquired by individual receive elements as described above were used to generate CMTUS images. For the simulated RF data, where the actual position of the arrays in space is known, an additional image, noted as 2-probes, was beam-formed by assuming a speed of sound of 1540 m/s and using the spatial location of the array elements. Note that, in the experimental case this is not possible because the actual position of the arrays in space is not accurately known a priori. Finally, the data corresponding to the sequence when the array T1 transmits and receives, i.e. T1R1, and noted here as 1-probe, was used as a base line for array performance, providing a point of comparison to the current coherent plane wave compounding method in both simulated and experimental scenarios. Note that, for all the cases except CMTUS, an assumed value of the speed of sound was used to beamform the data (1540 m/s for simulated data and 1450 m/s for experimental data).

In order to achieve a comparison between imaging modalities as fair as possible in terms of transmitted energy, the CMTUS and the 2-probes images are obtained by compounding only 6 different PW, while the 1 probe system images are generated compounding the total number of the transmit plane waves, i.e. 7 PW from −15° to 15°, in 5° step. In that vein, the CMTUS and 2-probes images are the results of compounding the RF data when the array T1 transmits PW at zero and positive angles) (0°,5°,10° and the array T2 transmits PW at zero and negative angles (0°,−5°,−10°). An even number of transmissions was set because the CMTUS optimization is based on a pair of transmissions, one per array. In addition, firing at opposite angles with the 2 arrays guarantees the CMTUS performance since an overlap of the isonated regions is mandatory to determine the relative probe-to-probe position.

For each resulting image, lateral resolution (LR), contrast and contrast-to-noise ratio 273 (CNR) were measured to quantify the impact of both the aperture size and the clutter. LR was calculated from the point-spread-function (PSF) of the middle point-like target. An axial-lateral plane for 2-D PSF analysis was chosen by finding the location of the peak value in the elevation dimension from the envelope-detected data. Lateral and axial PSF profiles were taken from the centre of the point target and aligned with the principal resolution directions. LR was then assessed by measuring the width of the PSF at the −6 dB level. The contrast and CNR were measured from the envelope-detected images. Contrast and CNR were calculated as:

Contrast=20 $\log_{10}(\mu_i/\mu_o)$ $CNR=|\mu_i-\lambda_o|/\sqrt{\mu_i^2+\mu_o^2}$.

Where $\mu_i$ and $\mu_o$ are the means of the signal inside and outside of the region, respectively. All image metrics were computed before log-compress transformation was applied.

Results
A. Simulation Results
Control Case: Conventional Aperture Imaging

The conventional aperture image, corresponding to the sequence when the array T1 transmits and receives, i.e. T1R1 (1-probe), provides the base line for imaging quality through the different scenarios.

Figure 17:
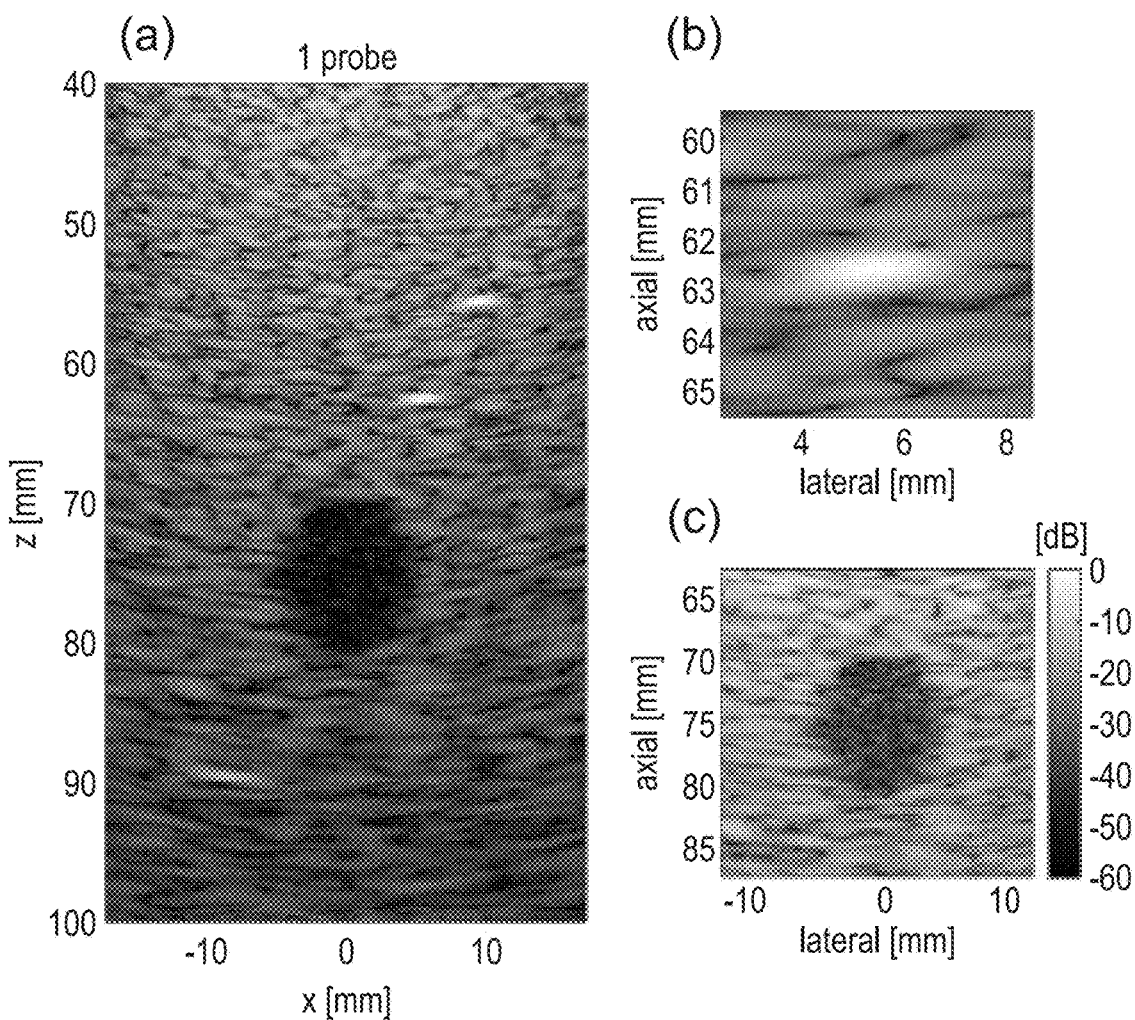
FIG. 17 is a conventional aperture image.

FIG. 17 illustrates the resulting image at 75 mm depth and without any aberrating to layer in the propagation medium. A speed of sound of 1540 m/s was used to reconstruct these images. The point target (FIG. 17(b)) has a lateral resolution of 1.78 mm and the lesion (FIG. 17(c)) is visible with a contrast of −16.78 dB and CNR of 0.846. Note that, while the lesion is easily identified from the background, it is difficult to delineate its edges.

CMTUS Discontinuous Effective Aperture

Figure 18:
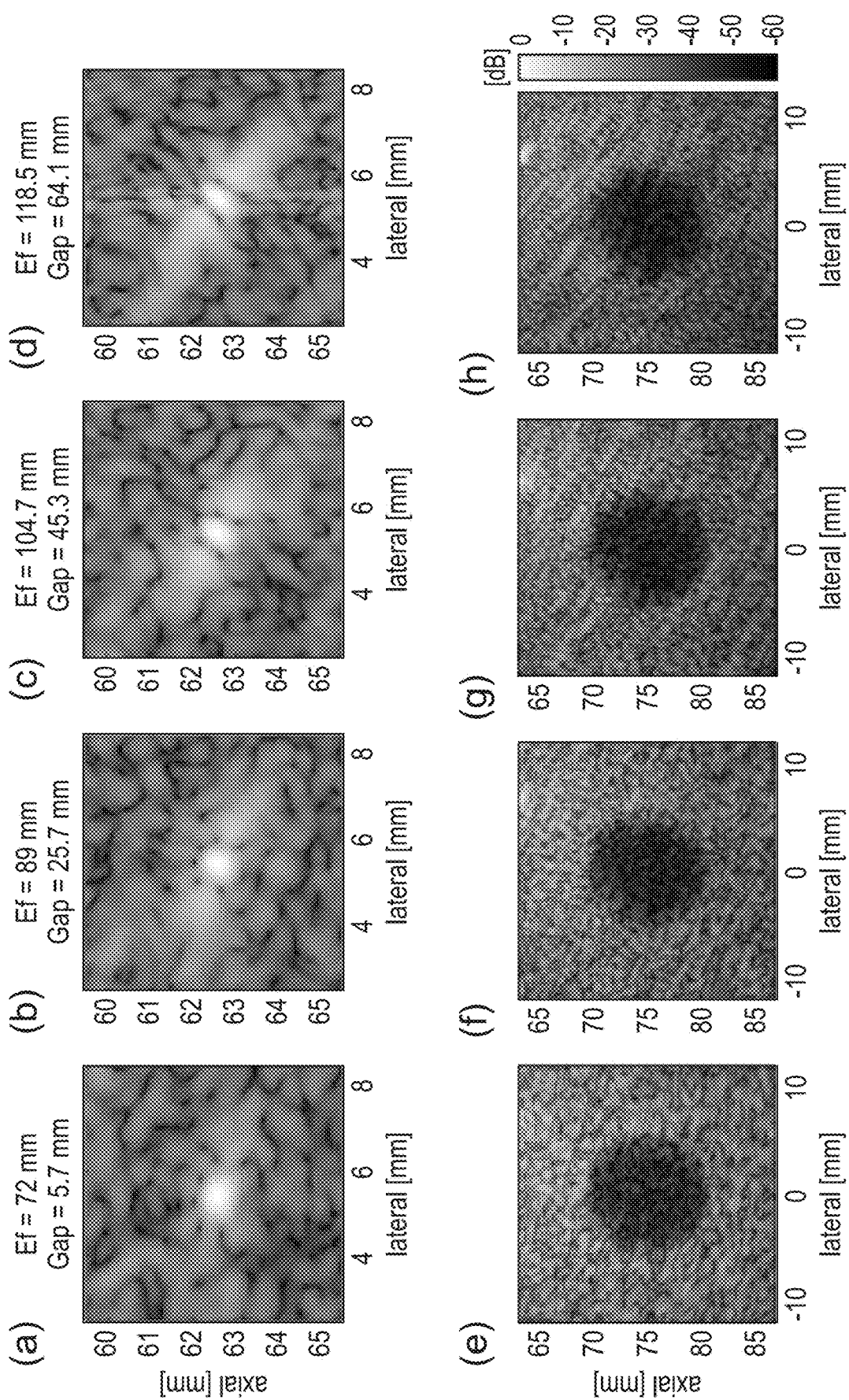
FIG. 18 illustrates a simulated PSF and lesion image from a non-aberrating medium for increasing effective aperture and gap of a CMTUS system.

FIG. 18 shows a simulated PSF and lesion images from the same non-aberrating medium and for increasing effective aperture and gap of the CMTUS system. It can be seen that, the PSF depends on the size of the effective aperture and the gap between the probes. As expected, the central lobe of the PSF reduces in width with increase in size of the effective aperture. However, while at extended apertures the width of the main lobe decreases, the amplitude of the side lobes increases with the corresponding gap in the aperture, affecting contrast as can be seen in the lesion images. The effects of the side lobes in the image quality can be seen in FIG. 18, where an effective aperture with a gap of 64.1 mm significantly raises the amplitude of the side lobes close to the main lobe's one and affects the lesion image.

Figure 19:
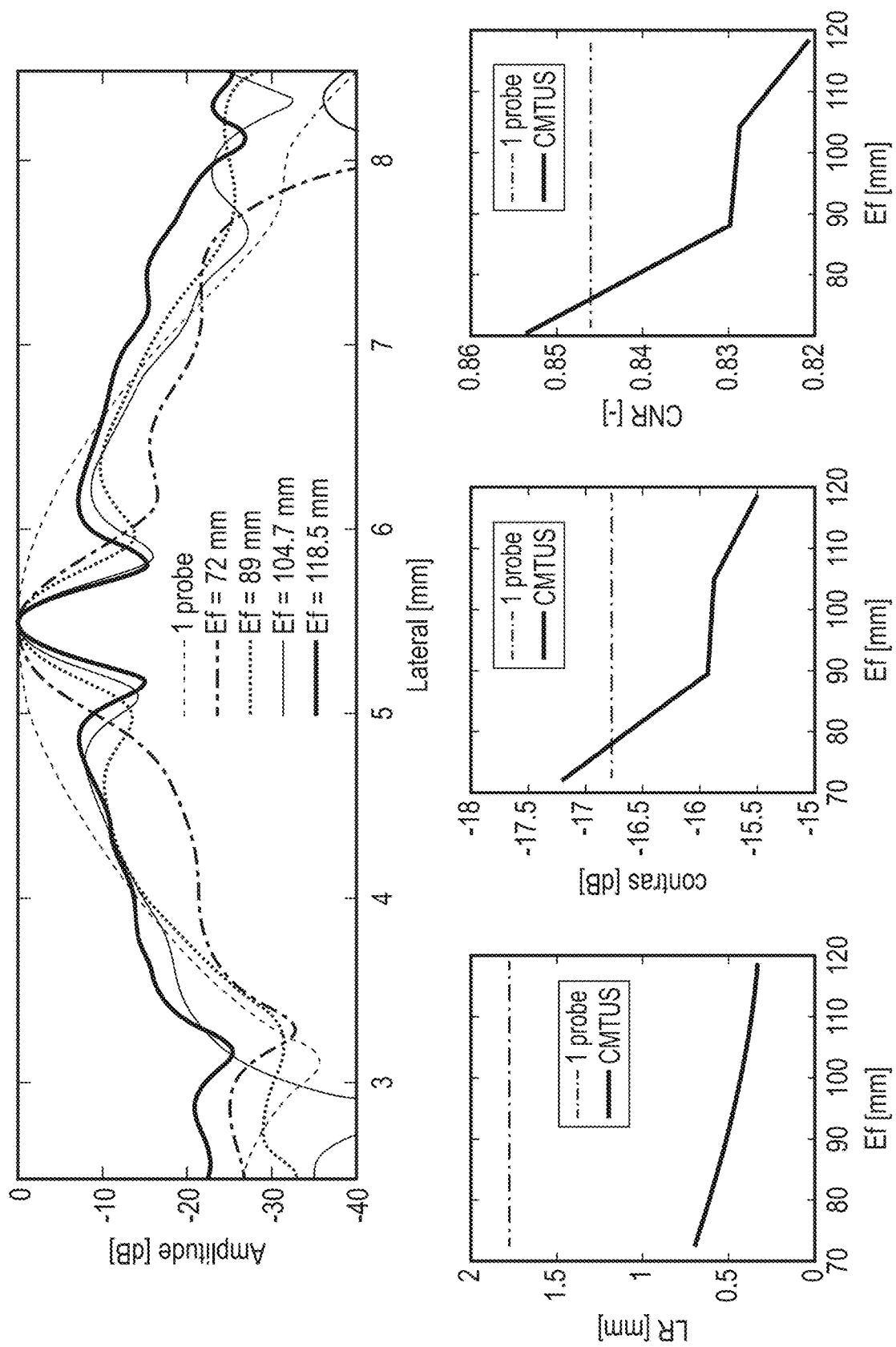
FIG. 19 compares computed image quality metrics of a CMTUS approach with a 1 probe system.

FIG. 19 compares corresponding computed image quality metrics (LR, contrast and CNR) as function of the obtained effective aperture. Results show that both the main lobe of the PSF and the lateral resolution decrease with larger effective aperture size. Since an increasing effective aperture represents also a larger gap between the probes, contrast and resolution follow opposite trends. In general, comparing with the 1-probe system, CMTUS produces the best lateral resolution in all the cases but shows degradation in contrast at the particular imaging depth of 75 mm. At the maximum effective aperture simulated, resolution is the best with 0.34 mm, while the contrast and CNR drop to a minimum of −15.51 dB and 0.82, respectively. FIG. 19 shows the lateral point spread functions extracted from FIG. 18 at the depth of peak point intensity and in the principal direction. Corresponding computed quality metrics as function of the effective aperture size in CMTUS: Lateral resolution (LR) measured at −6 dB from the lateral points spread function, contrast and contrast-to-noise-ratio (CNR) measured on FIG. 18.

CMTUS Image Penetration

Figure 20:
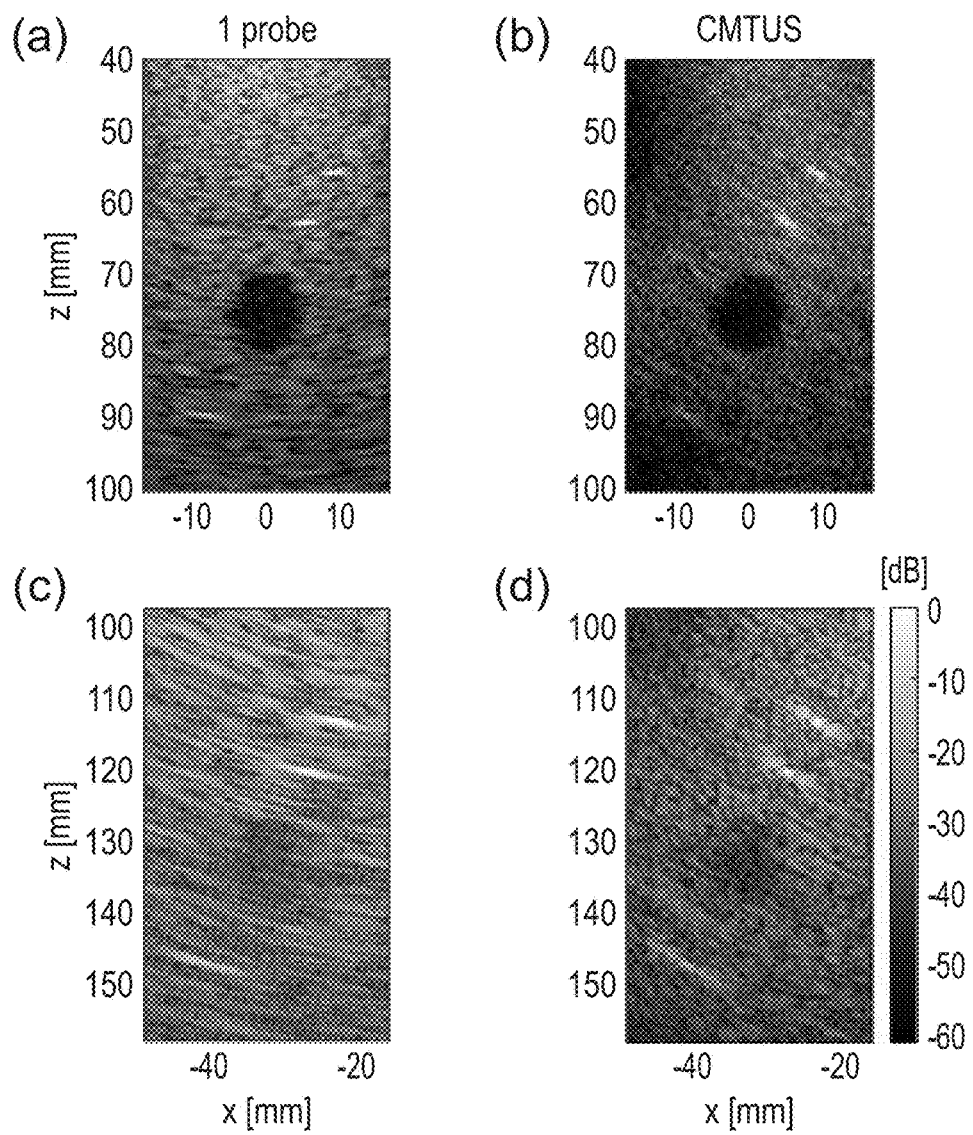
FIG. 20 compares CMTUS images with the 1-probe system at two different imaging depths (100 mm and 155 mm)

FIG. 20 compares CMTUS images with the 1-probe system at two different imaging depths (100 mm and 155 mm). Image degradation with depth is clearly observed in all the cases. However at larger depths the 1-probe shows a greater level of degradation. At the maximum imaging depth shown (155 mm), the point targets and the lesion can still be identified in the CMTUS image while in the 1-probe image is not obvious.

Figure 21:
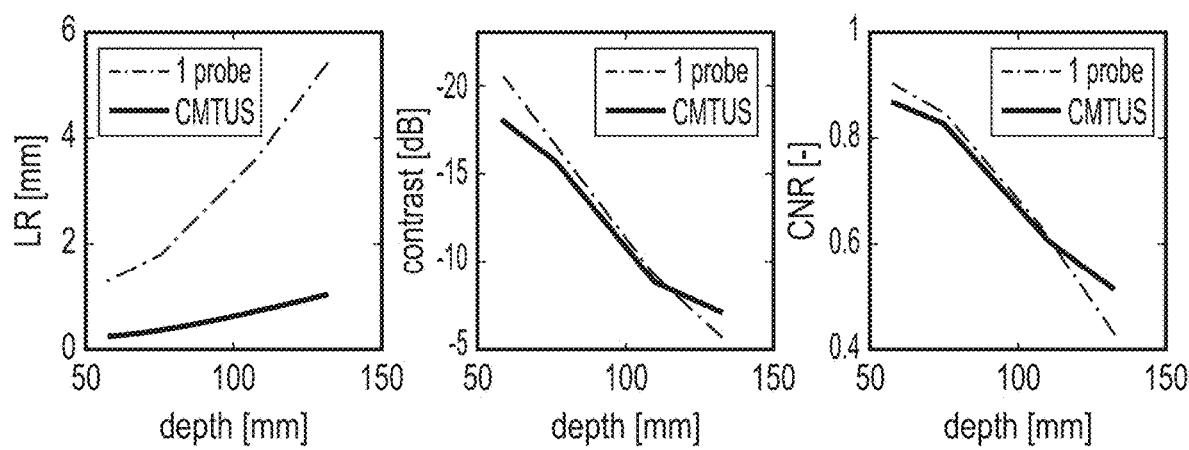
FIG. 21 compares computed quality metrics as a function of imaging depth.

FIG. 21 summarises computed image metrics as a function of imaging depth. As expected, in both systems, all image metrics worsen at larger imaging depths. Nevertheless, results show that their dependence on the imaging depth is different between the 1-probe and the CMTUS cases. The slope of the curve LR-depth is significantly higher in the 1-probe system than in the CMTUS method, which suggests that loss in resolution with imaging depth is faster at smaller apertures. While at reduced imaging depths (<100 mm) contrast and CNR seem to be affected in a similar way in both systems, the loss in contrast metrics are less accentuated in the CMTUS system at depths larger than 100 mm, where CMTUS method overcomes the performance of the 1-probe system not only in terms of resolution but also in contrast. The extended effective aperture created by CMTUS consequently increases the sensitivity of the imaging system, particularly at large imaging depths.

CMTUS Through Aberrating Media

Figure 22:
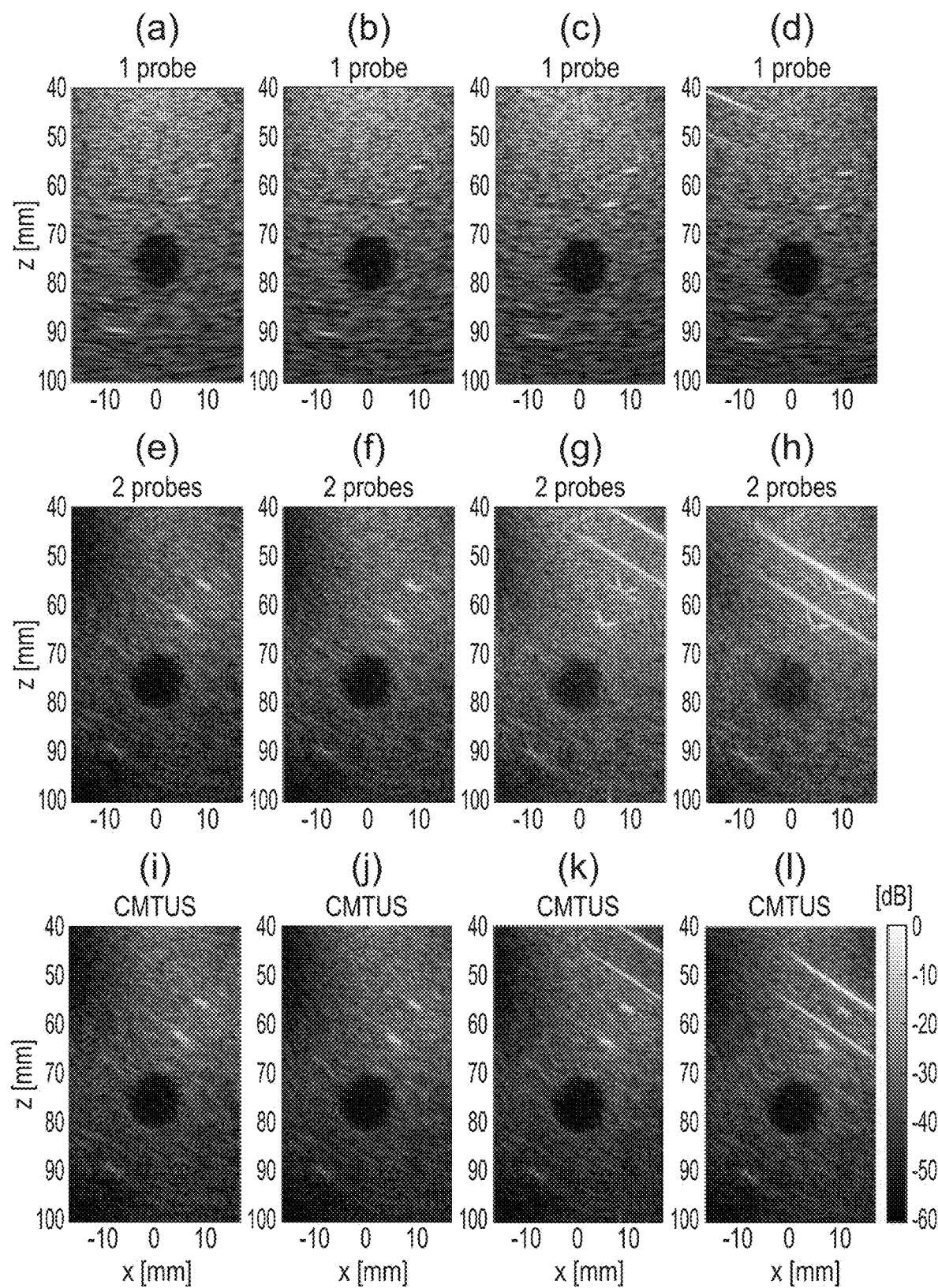
FIG. 22 is a comparison of simulated images acquired by a conventional aperture 1-probe (a-d), 2-probes (e-h) and CMTUS method (i-l) through aberrating layers of increasing thickness.

FIG. 22 is a comparison of simulated images acquired by a conventional aperture 1-probe (a-d), 2-probes (e-h) and CMTUS method (i-l) through aberrating layers of increasing thickness (thickness of fat layer increases from 0 mm, 10 mm, 25 mm to 35 mm). 1-probe images using 7 PW transmissions; 2-probes and CMTUS images using 6 PW transmissions.

FIG. 22 shows the simulated images for the control case (propagation medium only with soft tissue) and for imaging through aberrating layers of different thickness. The different methods, i.e. 1-probe, 2-probes and CMTUS are compared. It can be seen that, in the presence of aberration, the PSF and contrast of the 2-probes image significantly degrade when comparing with the control case. This effect is clearly seen in the point targets imaged through a fat layer of 35 mm thickness, where results show that if aberration is not corrected, extended apertures do not show benefits in terms of resolution. Indeed, in the presence of aberration, it is not possible to coherently reconstruct the image using the two separate transducers (2-probes system case).

Figure 23:
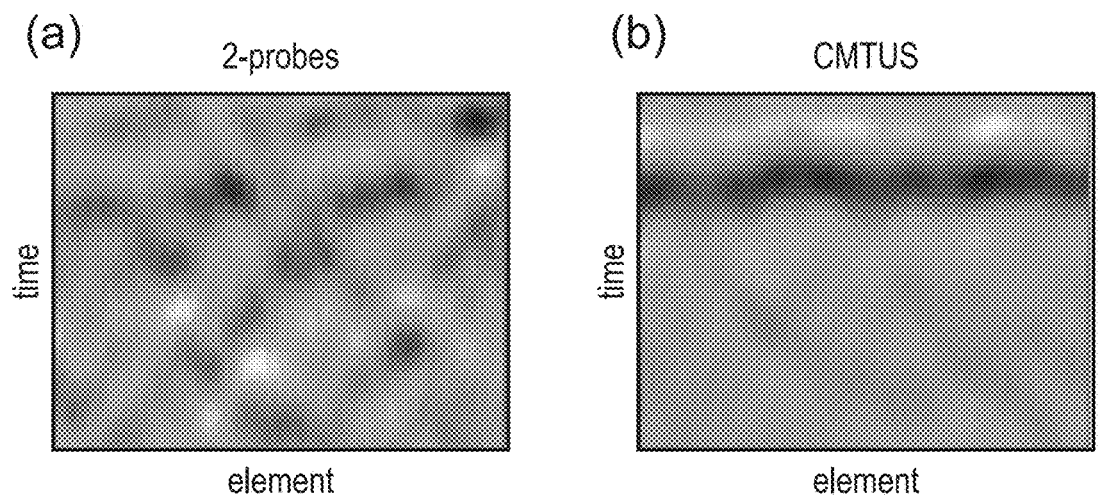
FIG. 23 shows simulated delayed RF data for a medium with a fat layer of 35 mm thickness.

FIG. 23 shows simulated delayed RF data for a medium with a fat layer of 35 mm thickness and backscattered from a point-like target, obtained by coherently adding the 4 delayed backscattered echoes from the same point-like target (T1R1; T1R2; T2R1; T2R2) and different beamforming parameters: FIG. 23(a) 2-probes; FIG. 23(b) CMTUS.

FIG. 23 shows an example of the delayed echos from the point-like target for the 2-probes and CMTUS cases, corresponding to a propagation medium with a fat layer of 35 mm thickness. These flat backscattered echoes are obtained by coherently adding the 4 delayed backscattered echoes from the same point-like target (T1R1; T1R2; T2R1; T2R2) and the corresponding beamforming parameters. It is worth pointing out that in the 2-probes case, the different echoes do not properly align, creating interference when coherently adding them together. However, after optimizing the beamforming parameters in the CMTUS, all echos align better and can be coherently added together, minimizing the aberrating consequences. Similar effects are seen in the anechoic lesion. While differences in the background speckle pattern are observed between the different imaging methods, a higher loss of contrast due to aberration can be appreciated only in the 2-probes images. Nevertheless, no significant changes in imaging quality because of aberration are appreciated in either the 1-probe or CMTUS systems. Although both systems are able to image through aberrating layers, they show clear differences. The CMTUS shows more detailed images than the 1-probe system. The speckle size is reduced and the different tissue layers are only visible in the CMTUS images.

Figure 24:
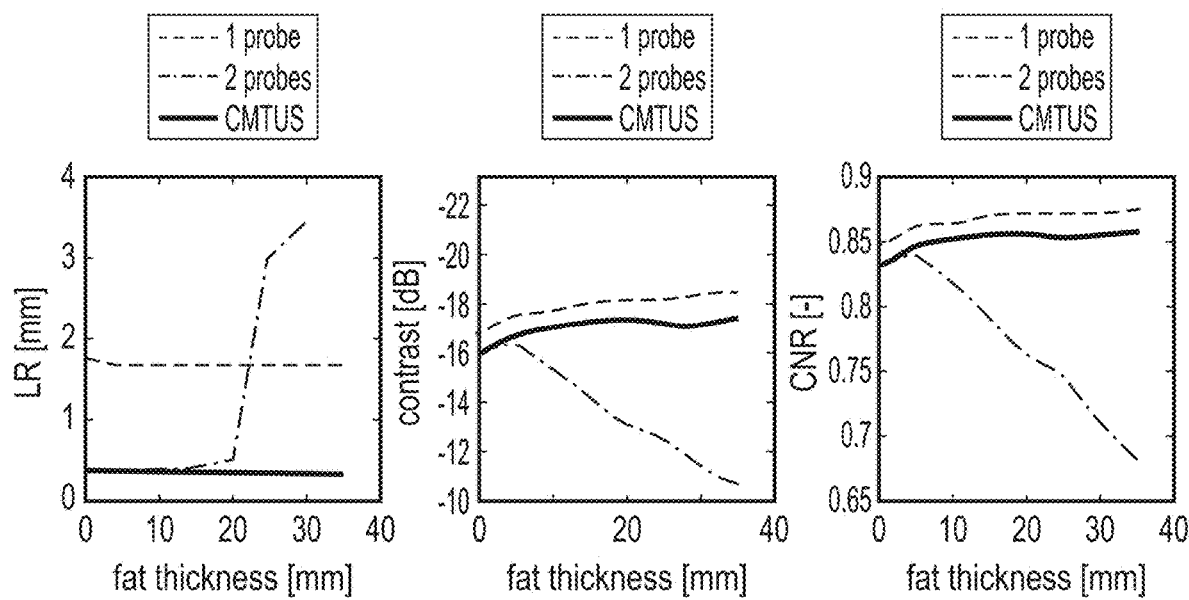
FIG. 24 is a comparison of computed quality metrics across different imaging methods.

FIG. 24 is a comparison of computed quality metrics across different imaging methods. FIG. 24 shows computed quality metrics, lateral resolution (LR), contrast and contrast-to-noise-ratio (CNR), as function of the clutter thickness (fat layer). Three different methods are compared: 1-probe coherent plane wave compound using 7 PW transmissions, 2-probes using 6 PW transmissions and CMTUS using 6 PW transmissions. Imaging metrics as function of fat layer thickness are shown. As expected, in the absence of aberration, resolution improves with increasing aperture size. In this case, the worst lateral resolution corresponds to 367 the 1-probe system with 1.78 mm, which is the one with smallest aperture size, while the 368 2-probes and CMTUS images are similar with 0.40 mm. The trends show that if aberration is not corrected, there are no significant improvements in the imaging metrics related to the aperture size for thicker thickness of fat layers. At clutter thickness larger than 10 mm, image quality of the system formed by 2 transducers without aberration correction (2-probes) is significantly degraded, while CMTUS imaging metrics are not affected by aberration errors, following the same trend as a conventional aperture (1-probe) and providing a constant value of resolution over clutter thickness without any significant loss of contrast. At the thickest fat layer simulated, resolution is 1.7 mm and 0.35 mm for the 1-probe and CTMUS images, respectively, while in the case of 2-probes images is no longer possible to reconstruct the point-target to measure resolution. Contrast and CNR also show a similar significant loss for the 2-probes image that presents a contrast of −10.84 dB and CNR of 0.69, while those values are significantly better for the 1-probe (−18.44 dB contrast and 0.87 CNR) and CMTUS (−17.41 dB contrast and 0.86 CNR) images.

Experimental Results

Coherent plane wave imaging with a conventional aperture imaging (using a single probe) provides the reference for image quality with and without the paraffin wax layer. To reconstruct these images the reference speed of sound in water of 1496 m/s was used and 7 PW were compounded.

Figure 25:
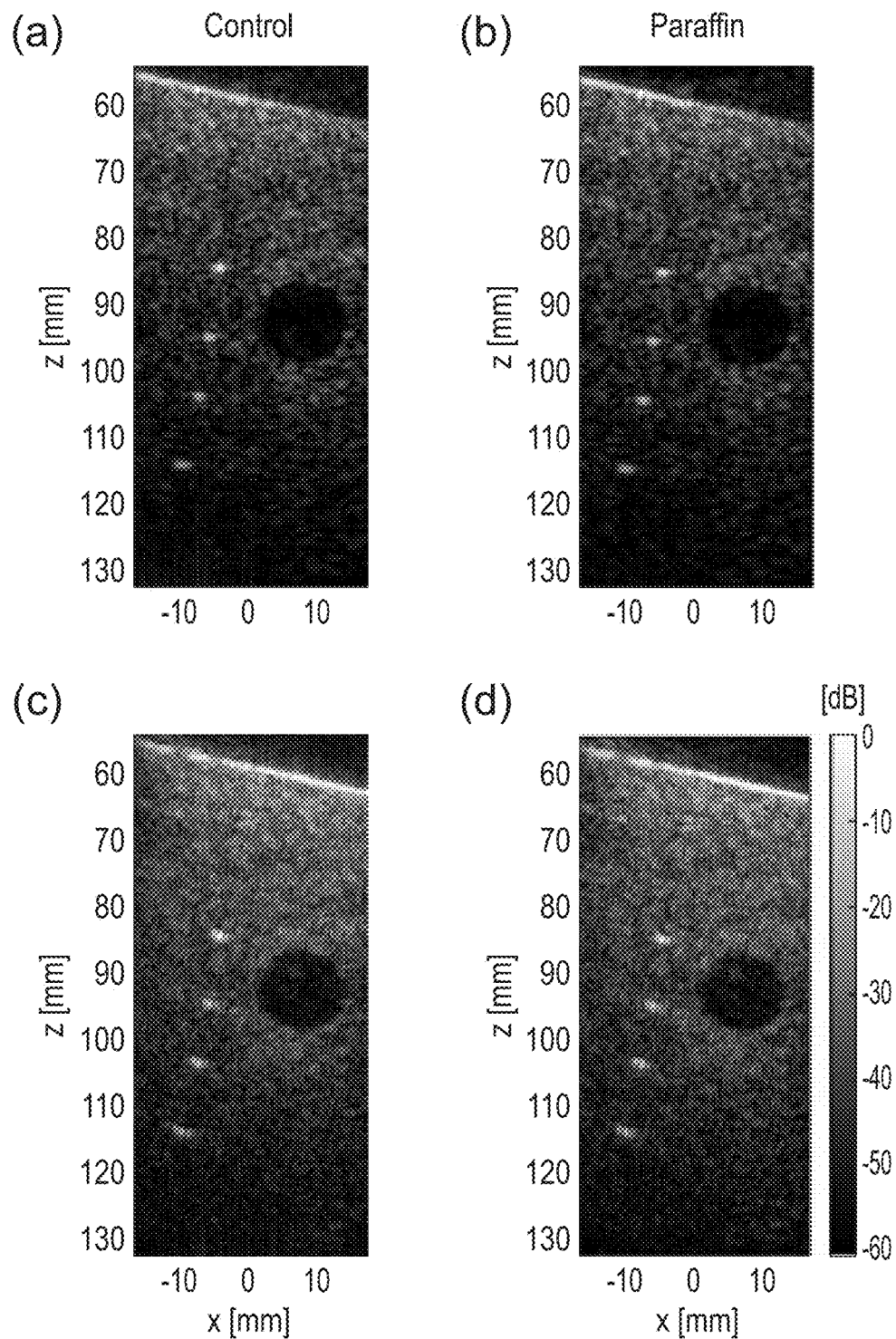
FIG. 25 shows a comparison of the phantom images acquired with 1-probe and CMTUS in the control case and through a paraffin wax sample.

FIG. 25 shows experimental images of a control (a,c) and the paraffin cases (b,d). Two different methods are compared: 1-probe coherent plane wave compound using 7 PW transmissions (a,b) and CMTUS using 6 PW transmissions (c,d). FIG. 25 shows a comparison of the phantom images acquired with 1-probe and CMTUS in the control case and through a paraffin wax sample. The CMTUS images were reconstructed using the optimum beamfoming parameters, which include the average speed of sound and compounding 6 PW. All images are shown in the same dynamic range of −60 dB. In both cases, 1-probe and CMTUS images, little variation is observed between the control and the paraffin images, which agree with the simulation results. The value of the optimum beamforming parameters used to reconstruct the CMTUS images is $\{c=1488.5$ m/s; $\theta_2=30.04°$; $r_2=[46.60, 12.33]$ mm$\}$ for the control case and $\{c=1482.6$ m/s, $\theta_2=30:00°$; $r_2=[46.70, 12.37]$ mm$\}$ for the paraffin. There are slight changes in all the values and a drop in the average speed of sound which agrees with the lower speed of propagation of sound of the paraffin wax.

Figure 26:
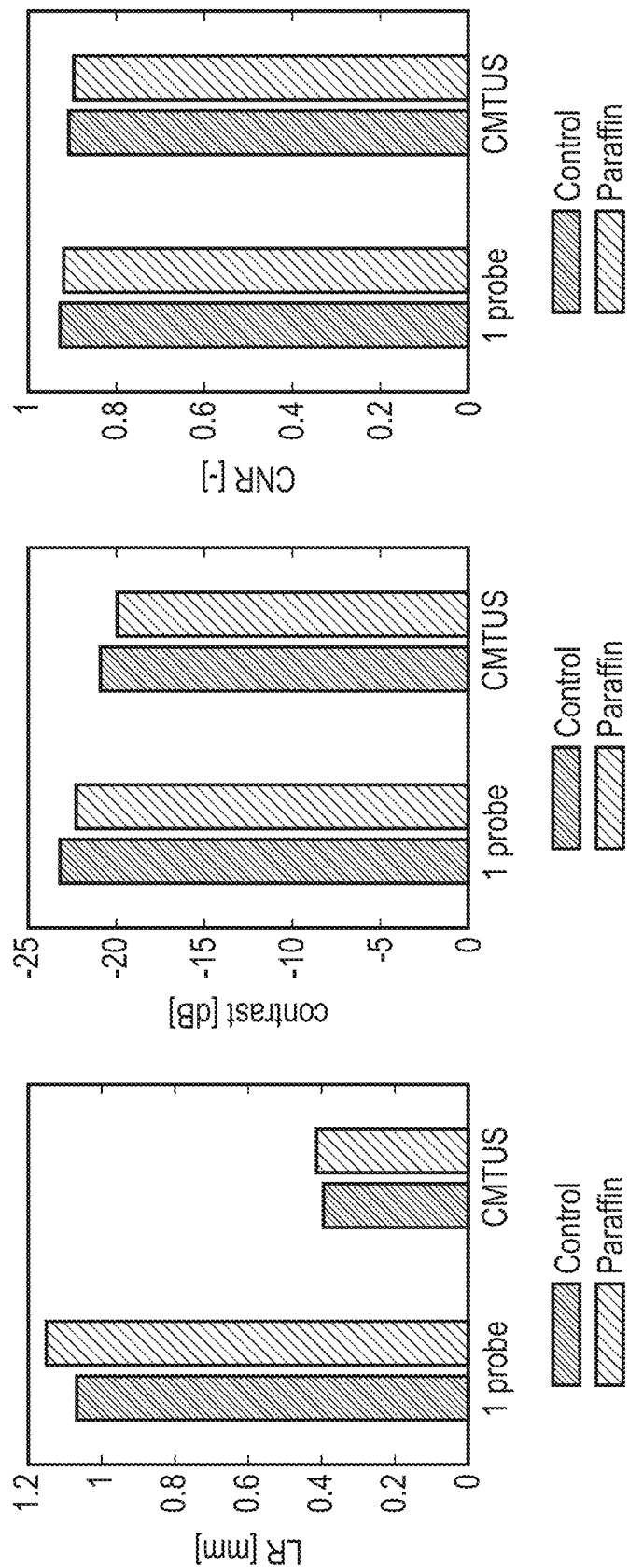
FIG. 26 shows a comparison of computed quality metrics, lateral resolution (LR), contrast and contrast-to-noise-ratio (CNR), experimentally measured for two different acquisition techniques.

FIG. 26 shows a comparison of computed quality metrics, lateral resolution (LR), contrast and contrast-to-noise-ratio (CNR), experimentally measured for two different acquisition techniques. Two different methods are compared: 1-probe coherent plane wave compound using 7 PW transmissions and CMTUS using 6 PW transmissions. FIG. 26 summarizes the computed image metrics for both the control and the paraffin cases. Little variation was observed in all the imaging metrics. Although minimum image degradation by aberrating layers was observed in the CMTUS, the overall image quality improved compared with the conventional single aperture and the observed image degradation follows the same trend.

Figure 27:
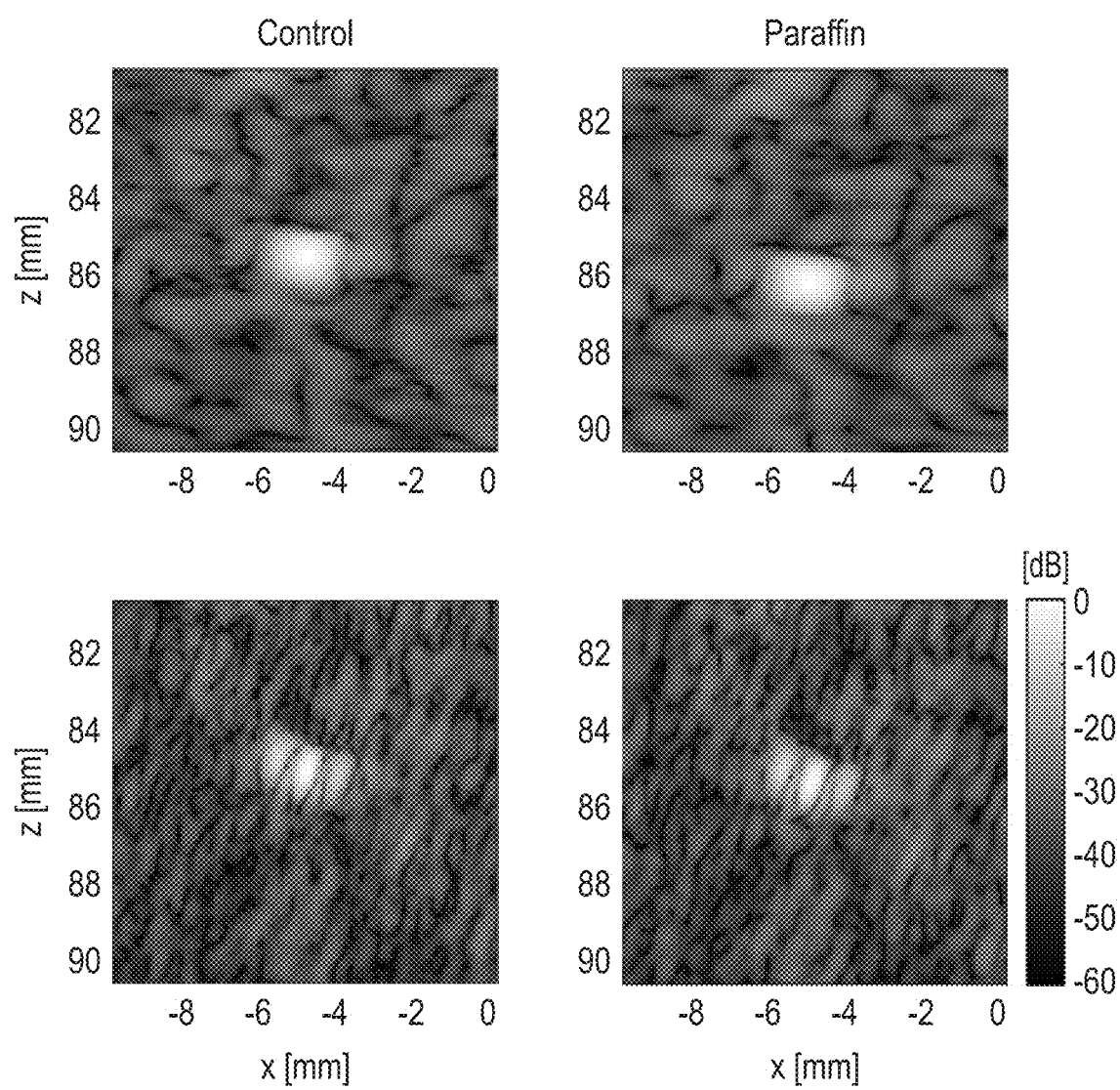
FIG. 27 compares experimental point target images.
Figure 27:
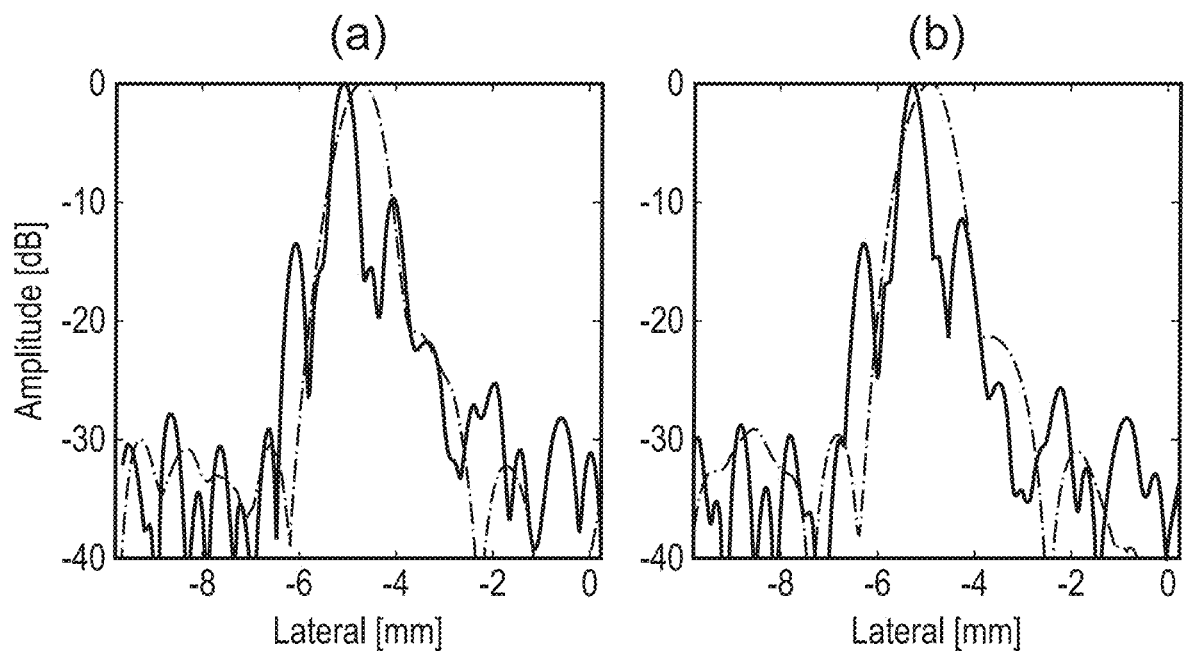

FIG. 27 compares experimental point target images. The first point target located at mm depth was described using its lateral PSF with and without the paraffin wax layer. No significant effects due to the aberration are observed in the PSF in any of the cases. The PSF shape is similar with and without the paraffin wax layer and agree with the one observed in simulations. In general, the CMTUS method leads to a PSF with significant narrower main lobe but also with side lobes of bigger amplitude than the 1-probe conventional imaging system.

FIG. 27 shows experimental point target images. Column (a) corresponds to the control and column (b) to the paraffin. First row corresponds to 1-probe system and middle row to CMTUS. Bottom row shows the corresponding lateral point spread functions for the two cases displayed: 1-probe system (dashed line) and CMTUS (solid line). 1-probe images using 7 PW transmissions. CMTUS images using 6 PW transmissions.

Figure 28:
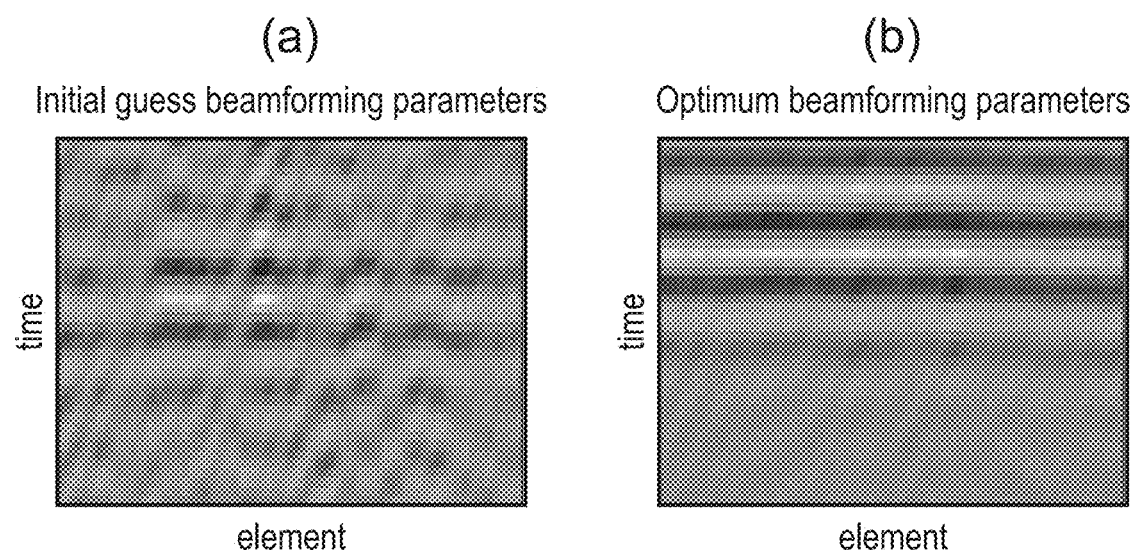
FIG. 28 shows experimental delayed RF data obtained using different beamforming parameters.

FIG. 28 shows the coherent summation of the delayed echos from the point-like target before and after optimization. The effects of the paraffin layer are clearly seen. When the beamforming parameters, including the averaged speed of sound, are optimized by the CMTUS methods, all echos align better, minimizing the aberrating paraffin effects. FIG. 28 shows experimental delayed RF data acquired from the phantom with the paraffin wax sample. CMTUS flat backscattered echo from a point-like target, obtained by coherently adding the 4 delayed backscattered echoes from the same point-like target (T1R1; T1R2; T2R1; T2R2) using different beamforming parameters: (a) initial guess values; (b) optimum values.

Discussion

The implications for imaging using the CMTUS method with two linear arrays have been investigated here with simulations and experiments. The analysis shows that the performance of the CMTUS depends on the relative location of the arrays, the CMTUS sensitivity increases with the imaging depth and the resulting extended aperture preserves in the presence of aberration. These findings show that, if the separation between transducers is limited, the extended effective aperture created by CMTUS confers benefits in resolution and contrast that improve image quality at large imaging depths and even in the presence of acoustic clutter imposed by tissue layers of different speed of sound. Unlike the improvement achieved in resolution, benefits in contrast are not so significant.

Simulation results suggest that, the discontinuous effective aperture may degrade contrast when the gap in the aperture is bigger than a few centimeters. In probe design, there is a requirement of half wavelength spacing between elements in order to avoid the occurrence of unwanted grating lobes in the array response. Moreover, previous studies indicated that, unlike resolution, contrast does not continue to increase uniformly at larger aperture sizes. Nevertheless, while the contrast may be degraded by big discontinuities in the aperture, the main lobe resolution continues to improve at larger effective apertures. Since the lesion detectability is a function of both the contrast and resolution overall there are benefits from extended aperture size, even when contrast is limited. A narrow main lobe allows fine sampling of high resolution targets, providing improved visibility of edges of clinically relevant targets. In addition, when imaging at larger depths, an extended aperture has the potential to improve the attenuation-limited image quality. In those challenging cases at large imaging depths, CMTUS shows improvements not only in resolution but also in contrast.

Results agree with the hypothesis that in the absence of aberration, the aperture size determines resolution. However, previous work suggests that despite predicted gains in resolution, there are practical limitations to the gains made at larger aperture sizes. Inhomogeneities caused changes in the side lobes and focal distance, limiting the improvement in resolution. The resulting degradation is primarily thought to be arrival time variation called phase aberration. The outer elements on a large transducer suffer from severe phase errors due to an aberrating layer of varying thickness, placing limits on the gains to be made from large arrays.

Findings presented here agree with these previous studies, and in the presence of aberration clutter, aperture size will be limited in practice. Nevertheless, the CMTUS method takes into account the average speed of sound in the medium and shows promise for extending the effective aperture beyond this practical limit imposed by the clutter. More accurate speed of sound estimation would improve beamforming and allow higher order phase aberration correction. However other challenges imposed by aberration still remain.

Both phase aberration and reverberation can be primary contributors to degraded image quality. While phase aberration effects are caused by variations in sound speed due to tissue inhomogeneity, reverberation is caused by multiple reflections within inhomogeneous medium, generating clutter that distorts the appearance of the wavefronts from the region of interest. For fundamental imaging, reverberations have been shown to be a significant cause of image quality degradation and are the principal reason why harmonic ultrasound imaging is better than fundamental imaging. It is envisaged that the role of redundancy in the large array in averaging multiple realizations of the reverberation signal may provide a mechanism for clutter reduction.

Whilst some choices made in the design of described experiments may not directly translate to clinical practice, it will be appreciated that they do not compromise the conclusions drawn from the results set out above. For example, the available H6J experimental setup drove the election of the frequency, which is higher than is traditionally used in abdominal imaging (1-2 MHz). In addition, although both the simulated and experimental phantoms are a simplistic model of real human tissue, they are able to capture the main potential causes that degrade ultrasound images, including attenuation, gross sound speed error, phase aberration, and reverberation clutter.

Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

REFERENCES

[1] M. Moshfeghi and R. Waag, "In vivo and in vitro ultrasound beam distortion measurements of a large aperture and a conventional aperture focussed transducer," Ultrasound in Medicine and Biology, vol. 14, no. 5, pp. 415-428, 1988.
[2] N. Bottenus, W. Long, M. Morgan, and G. Trahey, "Evaluation of large-aperture imaging through the ex vivo human abdominal wall," Ultrasound in medicine & biology, 2017.
[3] H. K. Zhang, A. Cheng, N. Bottenus, X. Guo, G. E. Trahey, and E. M. Boctor, "Synthetic tracked aperture ultrasound imaging: design, simulation, and experimental evaluation," Journal of Medical Imaging, vol. 3, no. 2, pp. 027 001-027 001, 2016.
[4] J. A. Jensen, O. Holm, L. Jerisen, H. Bendsen, S. I. Nikolov, B. G. Tomov, P. Munk, M. Hansen, K. Salomonsen, J. Hansen et al., "Ultrasound research scanner for real-time synthetic aperture data acquisition," IEEE transactions on ultrasonics, ferroelectrics, and frequency control, vol. 52, no. 5, pp. 881-891, 2005.

[5] N. Bottenus, W. Long, H. K. Zhang, M. Jakovljevic, D. P. Bradway, E. M. Boctor, and G. E. Trahey, "Feasibility of swept synthetic aperture ultrasound imaging," IEEE transactions on medical imaging, vol. 35, no. 7, pp. 1676-1685, 2016.

[6] H. K. Zhang, R. Finocchi, K. Apkarian, and E. M. Boctor, "Co-robotic synthetic tracked aperture ultrasound imaging with cross-correlation based dynamic error compensation and virtual fixture control," in Ultrasonics Symposium (IUS), 2016 IEEE International. IEEE, 2016, pp. 1-4.

[7] K. L. Gammelmark and J. A. Jensen, "2-d tissue motion compensation of synthetic transmit aperture images," IEEE Transactions on Ultrasonics, Ferroelectrics, and Frequency Control, vol. 61, no. 4, pp. 594-610, 2014.

[8] G. Montaldo, M. Tanter, J. Bercoff, N. Benech, and M. Fink, "Coherent plane-wave compounding for very high frame rate ultrasonography and transient elastography," IEEE Transactions on Ultrasonics, Ferroelectrics and Frequency Control, vol. 56, no. 3, pp. 489-506, 3 2009. [Online]. Available: http://ieeexplore.ieee.org/document/4816058/[9]

[9] A. W. Fitzgibbon, "Robust registration of 2d and 3d point sets," Image and Vision Computing, vol. 21, no. 13-14, pp. 1145-1153, 2003.

[10] R. Mallart and M. Fink, "The van cittert-zernike theorem in pulse echo measurements," The Journal of the Acoustical Society of America, vol. 90, no. 5, pp. 2718-2727, 1991.

[11] J. C. Lagarias, J. A. Reeds, M. H. Wright, and P. E. Wright, "Convergence properties of the nelder-mead simplex method in low dimensions," SIAM Journal on optimization, vol. 9, no. 1, pp. 112-147, 1998.

[12] E. Boni, L. Bassi, A. Dallai, F. Guidi, V. Meacci, A. Ramalli, S. Ricci, and P. Tortoli, "Ula-op 256: A 256-channel open scanner for development and real-time implementation of new ultrasound methods," IEEE transactions on ultrasonics, ferroelectrics, and frequency control, vol. 63, no. 10, pp. 1488-1495, 2016.

[13] M. Greenspan and C. E. Tschiegg, "Tables of the speed of sound in water," The Journal of the Acoustical Society of America, vol. 31, no. 1, pp. 75-76, 1959.

[14] R. A. Beasley, J. D. Stefansic, A. J. Herline, L. Guttierez, and R. L. Galloway, "Registration of ultrasound images," in Medical Imaging 1999: Image Display, vol. 3658. International Society for Optics and Photonics, 1999, pp. 125-133.

[15] M. E. Anderson and G. E. Trahey, "The direct estimation of sound speed using pulse-echo ultrasound," The Journal of the Acoustical Society of America, vol. 104, no. pp. 3099-3106, 1998.

[16] W. F. Walker and G. E. Trahey, "The application of k-space in pulse echo ultrasound," IEEE transactions on ultrasonics, ferroelectrics, and frequency control, vol. 45, no. 3, pp. 541-558, 1998.

[17] M. E. Anderson and G. E. Trahey, "A seminar on k-space applied to medical ultrasound," Department of Biomedical Engineering, Duke University, 2000.

[18] J. C. Lacefield, W. C. Pilkington, and R. C. Waag, "Distributed aberrators for emulation of ultrasonic pulse distortion by abdominal wall," Acoustics Research Letters Online, vol. 3, no. 2, pp. 47-52, 2002.

[19] J. Bamber and C. Hill, "Acoustic properties of normal and cancerous human liveri. dependence on pathological condition," Ultrasound in medicine & biology, vol. 7, no. 2, pp. 121-133, 1981.

[20] M. Imbault, A. Faccinetto, B.-F. Osmanski, A. Tissier, T. Deffieux, J.-L. Gennisson, V. Vilgrain, and M. Tanter, "Robust sound speed estimation for ultrasound-based hepatic steatosis assessment," Physics in Medicine and Biology, vol. 62, no. 9, p. 3582, 2017.

[21] L. Mercier, T. Langer, F. Lindseth, and L. D. Collins, "A review of calibration techniques for freehand 3-d ultrasound systems," Ultrasound in medicine & biology, vol. 31, no. 2, pp. 143-165, 2005.

[22] G. F. Pinton, G. E. Trahey, and J. J. Dahl, "Spatial coherence in human tissue: Implications for imaging and measurement," IEEE transactions on ultrasonics, ferroelectrics, and frequency control, vol. 61, no. 12, pp. 1976-1987, 2014.

[23] Y. Desailly, O. Couture, M. Fink, and M. Tanter, "Sono-activated ultrasound localization microscopy," Applied Physics Letters, vol. 103, no. 17, p. 174107, 2013.

[24] B. T. Fang, "Trilateration and extension to global positioning system navigation," Journal of Guidance, Control, and Dynamics, vol. 9, no. 6, pp. 715-717, 1986.

[25] E. Boni, L. Bassi, A. Dallai, F. Guidi, V. Meacci, A. Ramalli, S. Ricci, and P. Tortoli, "ULA-OP 256: A 256-channel open scanner for development and real-time implementation of new ultrasound methods," IEEE Transactions on Ultrasonics, Ferroelectrics and Frequency Control, vol. 63, no. 10, pp. 1488-1495, 2016.

[26] B. Denarie, T. A. Tangen, I. K. Ekroll, N. Rolim, H. Torp, T. Bj° astad, and L. Lovstakken, "Coherent plane wave compounding for very high frame rate ultrasonography of rapidly moving targets," IEEE Transactions on Medical Imaging, vol. 32, no. 7, pp. 1265-1276, 2013.

[27] R. A. Beasley, J. D. Stefansic, A. J. Herline, L. Guttierez, and R. L. Galloway, "Registration of ultrasound images," in Medical Imaging 1999: Image Display, vol. 3658. International Society for Optics and Photonics, 1999, pp. 125-133.

[28] W. F. Walker and G. E. Trahey, "The application of k-space in pulse echo ultrasound," IEEE Transactions on Ultrasonics, Ferroelectrics and Frequency Control, vol. 45, no. 3, pp. 541-558, 1998.

[29] S. W. Smith, R. F. Wagner, J. M. Sandrik, and H. Lopez, "Low contrast detectability and contrast/detail analysis in medical ultrasound," IEEE Transactions on Sonics and Ultrasonics, vol. 30, no. 3, pp. 164-173, 1983.

[30] M. E. Anderson and G. E. Trahey, "A seminar on k-space applied to medical ultrasound," Department of Biomedical Engineering, Duke University, 2000.

[31] M. Najafi, N. Afsham, P. Abolmaesumi, and R. Rohling, "A closed-form differential formulation for ultrasound spatial calibration: multi-wedge phantom," Ultrasound in Medicine & Biology, vol. 40, no. 9, pp. 2231-2243, 2014.

[32] E. Boctor, A. Viswanathan, M. Choti, R. H. Taylor, G. Fichtinger, and G. Hager, "A novel closed form solution for ultrasound calibration," in Biomedical Imaging: Nano to Macro, 2004. IEEE International Symposium on. IEEE, 2004, pp. 527-530.

[33] J. Provost, C. Papadacci, J. E. Arango, M. Imbault, M. Fink, J.-L. Gennisson, M. Tanter, and M. Pernot, "3D ultrafast ultrasound imaging in vivo," Physics in Medicine & Biology, vol. 59, no. 19, p. L1, 2014.

[34] M. Tanter and M. Fink, "Ultrafast imaging in biomedical ultrasound," IEEE Transactions on Ultrasonics, Ferroelectrics, and Frequency Control, vol. 61, no. 1, pp. 102-119, 2014.

[35] L. Mercier, T. Lange, F. Lindseth, and L. D. Collins, "A review of calibration techniques for freehand 3-D ultra-

[36] J. C. Lacefield, W. C. Pilkington, and R. C. Waag, "Distributed aberrators for emulation of ultrasonic pulse distortion by abdominal wall," Acoustics Research Letters Online, vol. 3, no. 2, pp. 47-52, 2002.

[37] J. Bamber and C. Hill, "Acoustic properties of normal and cancerous human liver-I. dependence on pathological condition," Ultrasound in Medicine & Biology, vol. 7, no. 2, pp. 121-133, 1981.

[38] M. Imbault, A. Faccinetto, B.-F. Osmanski, A. Tissier, T. Deffieux, J.-L. Gennisson, V. Vilgrain, and M. Tanter, "Robust sound speed estimation for ultrasound-based hepatic steatosis assessment," Physics in Medicine and Biology, vol. 62, no. 9, p. 3582, 2017.

[39] N. Bottenus and K. F. Üstüner, "Acoustic reciprocity of spatial coherence in ultrasound imaging," IEEE Transactions on Ultrasonics, Ferroelectrics, and Frequency Control, vol. 62, no. 5, p. 852, 2015.

[40] D.-L. Liu and R. C. Waag, "About the application of the van cittertzernike theorem in ultrasonic imaging," IEEE Transactions on Ultrasonics, Ferroelectrics, and Frequency Control, vol. 42, no. 4, pp. 590-601, 1995.

[41] W. F. Walker and G. E. Trahey, "Speckle coherence and implications for adaptive imaging," The Journal of the Acoustical Society of America, vol. 101, no. 4, pp. 1847-1858, 1997.

[42] D.-L. Liu and R. C. Waag, "Estimation and correction of ultrasonic wavefront distortion using pulse-echo data received in a two-dimensional aperture," IEEE Transactions on Ultrasonics, Ferroelectrics, and Frequency Control, vol. 45, no. 2, pp. 473-490, 1998.

[43] Y. L. Li and J. J. Dahl, "Coherent flow power doppler (CFPD): flow detection using spatial coherence beamforming," IEEE Transactions on Ultrasonics, Ferroelectrics, and Frequency Control, vol. 62, no. 6, pp. 1022-1035, 2015.

[44] M. A. Lediju, G. E. Trahey, B. C. Byram, and J. J. Dahl, "Shortlag spatial coherence of backscattered echoes: Imaging characteristics," IEEE Transactions on Ultrasonics, Ferroelectrics, and Frequency Control, vol. 58, no. 7, 2011.

[45] L. Peralta, K. Christensen-Jeffries, R. Paley, J. V. Hajnal, and R. J. Eckersley, "Microbubble contrast agents for coherent multi-transducer ultrasound imaging," in The 24st European Symposium on Ultrasound Contrast Imaging. ICUS, 2019, pp. 96-97.

[46] K. Christensen-Jeffries, R. J. Browning, M.-X. Tang, C. Dunsby, and R. J. Eckersley, "In vivo acoustic super-resolution and super-resolved velocity mapping using microbubbles," IEEE Transactions on Medical Imaging, vol. 34, no. 2, pp. 433-440, 2015.

[47] K. Christensen-Jeffries, S. Harput, J. Brown, P. N. Wells, P. Aljabar, C. Dunsby, M.-X. Tang, and R. J. Eckersley, "Microbubble axial localization errors in ultrasound super-resolution imaging," IEEE Transactions on Ultrasonics, Ferroelectrics, and Frequency Control, vol. 64, no. 11, pp. 1644-1654, 2017.

The invention claimed is:

1. An ultrasound method comprising:
providing, from each of two or more separate ultrasound transmitters, a signal into a coincident region;
receiving, at a receiving array, wavefronts representative of the provided signal from each of the two or more separate ultrasound transmitters after interaction of the provided signal with a medium located within the coincident region;
selecting one or more parameters which together act to define a relative location of each of the two or more separate ultrasound transmitters in space;
analyzing the received wavefronts to make an initial guess at the selected one or more parameters; and
performing an iterative process to refine the initial guess at the selected one or more parameters, the iterative process operating to refine the initial guess by:
increasing a correlation between the received wavefronts;
using the refined parameters to determine a relative spatial position of the two or more separate ultrasound transmitters; and
performing a coherent signal combination of the received wavefronts received at the receiving array based on the provided signal from each of the two or more separate ultrasound transmitters after interaction of the provided signal with the medium located within the coincident region based upon the determined relative spatial position of each of the two or more separate ultrasound transmitters.

2. The ultrasound method according to claim 1, comprising stopping the iterative process in accordance with a stopping criteria comprising one or more of: a selected number of iterations; a measure of fit passing a selected threshold; a maxima or minima or rate of change of a fit parameter reaching a plateau.

3. The ultrasound method according to claim 1, comprising receiving the initial guess of the selected one or more parameters from one or more orientation sensors associated with each of the two or more separate ultrasound transmitters.

4. The ultrasound method according to claim 1, wherein the one or more parameters comprise one or more of: a location of one or more scatterer located within the medium located within the coincident region; a relative angle between the two or more separate ultrasound transmitters; a relative distance of the two or more separate ultrasound transmitters from the receiving array; or a speed of sound within the medium located within the coincident region.

5. An ultrasound apparatus comprising:
two or more separate ultrasound transmitters positioned to transmit a signal into a coincident region,
a receiving array for receiving a wavefront representative of a transmitted signal from each of the two or more separate ultrasound transmitters after interaction of the transmitted signal with a medium located within the coincident region;
location processing logic to:
select one or more parameters which together act to define a relative location of each of the two or more separate ultrasound transmitters in space;
analyze each of the received wavefronts to make an initial guess at the selected one or more parameters;
perform an iterative process to refine the initial guess at the selected one or more parameters, the iterative process operating to refine the initial guess by increasing a correlation between the received wavefronts; and
determine a relative spatial position of each of the two or more separate ultrasound transmitters; and
signal combination logic to use the determined relative spatial position of each of the two or more separate ultrasound transmitters to perform coherent signal combination of the received wavefronts received at the receiving array from each of the two or more separate ultrasound transmitters after interaction of the transmitted signal with the medium located within the coincident region.

6. The ultrasound apparatus according to claim 5, wherein the two or more separate ultrasound transmitters are located such that their signal volumes at least partly overlap within the coincident region.

7. The ultrasound apparatus according to claim 5, wherein the two or more separate ultrasound transmitters provide the transmitted signal into the coincident region substantially concurrently.

8. The ultrasound apparatus according to claim 5, wherein the two or more separate ultrasound transmitters provide the transmitted signal into the coincident region consecutively.

9. The ultrasound apparatus according to claim 5, wherein the transmitted signal from each of the two or more separate ultrasound transmitters comprises a plane wave.

10. The ultrasound apparatus according to claim 5, wherein the ultrasound apparatus further comprises:
   an additional receiving array to receive the wavefront representative of the transmitted signal from each of the two or more separate ultrasound transmitters after interaction of the transmitted signal with the medium located within the coincident region;
   wherein the location processing logic analyzes each of the received wavefronts received at the receiving array and the additional receiving array to determine the relative spatial position of each of the two or more separate ultrasound transmitters; and
   wherein the signal combination logic uses the determined relative spatial position of each of the two or more separate ultrasound transmitters from the receiving array and the additional receiving array to perform coherent image reconstruction of the medium located within the coincident region by combining the received wavefronts.

11. The ultrasound apparatus according to claim 10, wherein at least one of the two or more separate ultrasound transmitters and one or more of the receiving array and the additional receiving array are co-located to form an ultrasound transducer.

12. A non-transitory computer readable storage medium storing instructions thereon that, when executed by at least one processor, cause a computer device to:
   provide, from each of two or more separate ultrasound transmitters, a signal into a coincident region;
   receive, at a receiving array, wavefronts representative of the provided signal from each of the two or more separate ultrasound transmitters after interaction of the provided signal with a medium located within the coincident region;
   select one or more parameters which together act to define a relative location of each of the two or more separate ultrasound transmitters in space;
   analyze the received wavefronts to make an initial guess at the selected one or more parameters; and
   perform an iterative process to refine the initial guess at the selected one or more parameters, the iterative process operating to refine the initial guess by:
      increasing a correlation between the received wavefronts;
      using the refined parameters to determine a relative spatial position of the two or more separate ultrasound transmitters, and
      performing a coherent signal combination of the received wavefronts received at the receiving array based on the provided signal from each of the two or more separate ultrasound transmitters after interaction of the provided signal with the medium located within the coincident region based upon the determined relative spatial position of each of the two or more separate ultrasound transmitters.

13. The non-transitory computer readable storage medium of claim 12, wherein the one or more parameters comprise one or more of: a location of one or more scatterer located within the medium located within the coincident region; a relative angle between the two or more separate ultrasound transmitters; a relative distance of the two or more separate ultrasound transmitters from the receiving array; or a speed of sound within the medium located within the coincident region.

* * * * *